US012714838B2

(12) United States Patent
Kim

(10) Patent No.: US 12,714,838 B2
(45) Date of Patent: Aug. 25, 2026

(54) MICRONEEDLE ASSEMBLY

(71) Applicant: Ticona LLC, Florence, KY (US)

(72) Inventor: Young Shin Kim, Cincinnati, OH (US)

(73) Assignee: Ticona LLC, Florence, KY (US)

(*) Notice: Subject to any disclaimer, the term of this patent is extended or adjusted under 35 U.S.C. 154(b) by 1494 days.

(21) Appl. No.: 17/235,976

(22) Filed: Apr. 21, 2021

(65) Prior Publication Data

US 2021/0330951 A1 Oct. 28, 2021

Related U.S. Application Data

(60) Provisional application No. 63/034,429, filed on Jun. 4, 2020, provisional application No. 63/016,560, filed on Apr. 28, 2020.

(51) Int. Cl.

| | |
|---|---|
| ***A61M 37/00*** | (2006.01) |
| ***A61B 5/00*** | (2006.01) |
| ***A61B 5/145*** | (2006.01) |
| ***A61B 17/20*** | (2006.01) |

(52) U.S. Cl.

CPC ..... *A61M 37/0015* (2013.01); *A61B 5/14503* (2013.01); *A61B 5/14532* (2013.01); *A61B 5/685* (2013.01); *A61B 17/205* (2013.01); *A61M 2037/0023* (2013.01); *A61M 2037/0038* (2013.01); *A61M 2037/0046* (2013.01); *A61M 2037/0061* (2013.01)

(58) Field of Classification Search

CPC ...... A61M 37/0015; A61M 2037/0023; A61M 2037/0038; A61M 2037/0046; A61M 2037/0061; A61B 5/14503; A61B 5/14532; A61B 5/685; A61B 17/205

See application file for complete search history.

(56) References Cited

U.S. PATENT DOCUMENTS

| | | | |
|---|---|---|---|
| 4,161,470 | A | 7/1979 | Calundann |
| 4,837,798 | A | 6/1989 | Cohen et al. |
| 5,078,700 | A | 1/1992 | Lambert et al. |
| 5,151,231 | A | 9/1992 | Lambert et al. |
| 5,456,875 | A | 10/1995 | Lambert |
| 5,616,680 | A | 4/1997 | Linstid, III |
| 5,879,326 | A | 3/1999 | Godshall et al. |
| 5,932,315 | A | 8/1999 | Lum et al. |
| 6,102,933 | A | 8/2000 | Lee et al. |
| 6,114,492 | A | 9/2000 | Linstid, III et al. |
| 6,454,755 | B1 | 9/2002 | Godshall |
| 6,471,903 | B2 | 10/2002 | Sherman et al. |
| 6,514,611 | B1 | 2/2003 | Shepherd et al. |
| 6,663,820 | B2 | 12/2003 | Arias et al. |
| 6,749,792 | B2 | 6/2004 | Olson |
| 6,767,496 | B1 | 7/2004 | Jensen et al. |
| 6,780,370 | B2 | 8/2004 | Sugimoto et al. |
| 6,815,360 | B1 | 11/2004 | Canham et al. |
| 6,881,203 | B2 | 4/2005 | Delmore et al. |
| 6,899,838 | B2 | 5/2005 | Lastovich |
| 6,908,453 | B2 | 6/2005 | Fleming et al. |
| 6,924,087 | B2 | 8/2005 | Yeshurun et al. |
| 7,004,928 | B2 | 2/2006 | Aceti et al. |
| 7,045,365 | B2 | 5/2006 | Coyne et al. |
| 7,070,727 | B2 | 7/2006 | Calhoun |
| 7,168,605 | B2 | 1/2007 | Walak |
| 7,288,394 | B2 | 10/2007 | Ostuni et al. |
| 7,291,497 | B2 | 11/2007 | Holmes et al. |
| 7,455,654 | B2 | 11/2008 | Cormier et al. |
| 7,467,498 | B2 | 12/2008 | Fontaine |
| 7,497,980 | B2 | 3/2009 | Xu et al. |
| 7,648,484 | B2 | 1/2010 | Yeshurun et al. |
| 7,658,728 | B2 | 2/2010 | Yuzhakov |
| 7,678,128 | B2 | 3/2010 | Boyle et al. |
| 7,785,301 | B2 | 8/2010 | Yuzhakov |
| 7,914,480 | B2 | 3/2011 | Cleary et al. |
| 7,964,171 | B2 | 6/2011 | Sugimoto et al. |
| 8,052,633 | B2 | 11/2011 | Kendall |
| 8,088,321 | B2 | 1/2012 | Ferguson et al. |
| 8,101,402 | B2 | 1/2012 | Holmes |
| 8,202,697 | B2 | 6/2012 | Holmes |
| 8,236,231 | B2 | 8/2012 | Ferguson et al. |
| 8,246,893 | B2 | 8/2012 | Ferguson et al. |
| 8,303,518 | B2 | 11/2012 | Aceti et al. |

(Continued)

FOREIGN PATENT DOCUMENTS

| | | | |
|---|---|---|---|
| AU | 2014200648 | A1 | 2/2014 |
| AU | 2014202446 | A1 | 5/2014 |

(Continued)

OTHER PUBLICATIONS

Bigham et al.; Technical Paper LCP Introduction to Liquid Crystal Polymers; Zeus Industrial Products; 2016 (Year: 2016).*

Is polyvinylidene a tribiologic additive material—Google Search (Year: 2025).*

Parathryroid hormone mw—Google Search (Year: 2025).*

Virus vaccines—Google Search (Year: 2025).*

"3M Drug Delivery System announces Collaboration with Panacea Pharmaceuticals on New Cancer Vaccine", 3M Science, Applied to Life, Jan. 10, 2017, 2 pages.

"3M Proves Efficacy of Hollow Microstructured Transdermal System", Business Wire, Nov. 18, 2008, 2 pages.

(Continued)

*Primary Examiner* — Robert A Wax

*Assistant Examiner* — John W Lippert, III

(74) *Attorney, Agent, or Firm* — Dority & Manning, P.A.

(57) ABSTRACT

A microneedle assembly that is capable of delivering a drug compound (e.g., vaccine) and/or detecting the presence of an analyte is provided. The assembly comprises at least one microneedle extending outwardly from a support. The microneedle includes a polymer composition containing a thermoplastic polymer having a melting temperature of about 250° C. or more. The polymer composition exhibits a melt viscosity of about 100 Pa-s or less and a tensile elongation of about 5% or less.

52 Claims, 3 Drawing Sheets

(56) References Cited

U.S. PATENT DOCUMENTS 8,324,307 B2 * 12/2012 Harder .................... C08L 77/06 524/514
8,361,022 B2 1/2013 Ameri et al.
8,449,807 B2 5/2013 Ferguson et al.
8,483,595 B2 7/2013 Ishii et al.
8,585,682 B2 11/2013 Mitra et al.
8,628,493 B2 1/2014 Ahn et al.
8,636,696 B2 1/2014 Ross et al.
8,668,675 B2 3/2014 Chase et al.
8,668,867 B2 3/2014 Scalzo et al.
8,696,637 B2 4/2014 Ross
8,700,122 B2 4/2014 Cordero et al.
8,734,697 B2 5/2014 Chen et al.
8,821,446 B2 9/2014 Trautman et al.
8,821,779 B2 9/2014 Ferguson et al.
8,858,807 B2 10/2014 DeVoe et al.
8,883,015 B2 11/2014 Kendall et al.
8,900,194 B2 12/2014 Clarke et al.
8,906,486 B2 12/2014 Fontaine
8,920,375 B2 12/2014 Gonnelli
8,920,817 B2 12/2014 Ameri et al.
8,956,548 B2 2/2015 Clapp et al.
9,012,011 B2 4/2015 Ferguson et al.
9,104,100 B2 8/2015 Redinger et al.
9,114,238 B2 8/2015 Singh et al.
9,131,884 B2 9/2015 Holmes et al.
9,220,678 B2 12/2015 Kendall et al.
9,244,202 B2 1/2016 Huang et al.
9,283,365 B2 3/2016 Kendall et al.
9,289,925 B2 3/2016 Ferguson et al.
9,297,094 B2 3/2016 Zussman
9,302,903 B2 4/2016 Park et al.
9,320,878 B2 4/2016 Jin
9,339,956 B2 5/2016 Rendon
9,347,143 B2 5/2016 Wang et al.
9,375,399 B2 6/2016 Douroumis
9,387,000 B2 7/2016 Corrie et al.
9,408,947 B2 8/2016 Grandt et al.
9,464,368 B2 10/2016 Zussman et al.
9,469,919 B2 10/2016 Kuhn et al.
9,486,770 B2 11/2016 Trau
9,498,524 B2 11/2016 Ghartey-Tagoe et al.
9,511,525 B2 12/2016 Ferguson et al.
9,522,262 B2 12/2016 Ross
9,522,263 B2 12/2016 Ross
9,526,883 B2 12/2016 Ross
9,526,884 B2 12/2016 Chen
9,539,418 B2 1/2017 Quan et al.
9,540,684 B2 1/2017 Mahmood et al.
9,545,507 B2 1/2017 Ross
9,549,756 B2 1/2017 Sauter et al.
9,550,053 B2 1/2017 Ross
9,572,969 B2 2/2017 Kendall
9,592,362 B2 3/2017 Chen et al.
9,603,562 B2 3/2017 Aceti et al.
9,636,490 B2 5/2017 Masaoka et al.
9,675,675 B2 6/2017 Zhang et al.
9,675,789 B2 6/2017 Chen et al.
9,687,641 B2 6/2017 Singh et al.
9,693,950 B2 7/2017 Determan et al.
9,737,247 B2 8/2017 Wang et al.
9,758,778 B2 9/2017 Chen et al.
9,795,774 B2 10/2017 Takada et al.
9,795,775 B2 10/2017 Baker et al.
9,808,377 B2 11/2017 Mitra et al.
9,834,218 B2 12/2017 Rovik et al.
9,861,801 B2 1/2018 Baker et al.
9,888,932 B2 2/2018 Kendall
9,895,521 B2 2/2018 Mohr
9,943,673 B2 4/2018 Kendall et al.
9,944,019 B2 4/2018 Falo, Jr. et al.
9,962,536 B2 5/2018 Baker et al.
9,974,935 B2 5/2018 Toyohara et al.
9,982,356 B2 5/2018 Wang et al.
9,993,423 B2 6/2018 Quan et al.
10,010,499 B2 7/2018 Chiang et al.
10,010,707 B2 7/2018 Colburn et al.
10,022,322 B2 7/2018 Kendall et al.
10,067,269 B2 9/2018 Lee et al.
10,099,043 B2 10/2018 Berry et al.
10,105,524 B2 10/2018 Meyer et al.
10,112,979 B2 10/2018 O'Hagan
10,117,990 B2 11/2018 Castracane et al.
10,130,283 B2 11/2018 Holmes et al.
10,135,907 B2 11/2018 Palanivel et al.
10,154,957 B2 12/2018 Zhang et al.
10,155,334 B2 * 12/2018 Rendon .................. B29C 45/77
10,195,410 B2 2/2019 Jin
10,201,691 B2 2/2019 Berry et al.
10,207,094 B2 2/2019 Stoeber et al.
10,232,157 B2 3/2019 Berry et al.
10,232,159 B2 3/2019 Birchall et al.
10,259,922 B2 4/2019 Zare et al.
10,272,233 B2 4/2019 Kang et al.
10,300,260 B2 5/2019 Wirtanen et al.
10,377,062 B2 8/2019 Kaspar et al.
10,384,047 B2 8/2019 Simmers
10,398,885 B2 9/2019 Frits et al.
10,449,344 B2 10/2019 Canovas et al.
10,463,608 B2 11/2019 D'Souza
10,537,518 B2 1/2020 Jung et al.
10,549,079 B2 2/2020 Burton et al.
10,576,257 B2 3/2020 Berry et al.
10,623,472 B2 4/2020 Palanivel et al.
10,646,702 B2 5/2020 Sul et al.
10,668,260 B2 6/2020 Omachi et al.
10,668,261 B2 6/2020 Hochi et al.
10,675,452 B2 6/2020 Syrek et al.
10,682,504 B2 6/2020 Kato
10,716,925 B2 7/2020 Baek
10,772,550 B2 9/2020 Aceti et al.
10,791,571 B2 9/2020 Kim
10,792,857 B2 10/2020 Desimone et al.
10,799,691 B2 10/2020 Uemura et al.
10,814,115 B2 10/2020 Traverso et al.
10,828,478 B2 11/2020 McAllister et al.
10,850,082 B2 12/2020 Faraji Rad et al.
10,933,029 B2 3/2021 Liu
10,933,173 B2 3/2021 Kaplan et al.
10,940,301 B2 3/2021 McAllister et al.
10,967,164 B2 4/2021 Park et al.
10,973,757 B2 4/2021 Tankovich
10,980,991 B2 4/2021 Lee et al.
10,980,992 B2 4/2021 Gu et al.
10,987,502 B2 4/2021 Fudoji et al.
10,994,111 B2 5/2021 Quan et al.
10,995,366 B2 5/2021 Mahmood
11,013,670 B2 5/2021 Kim et al.
11,040,182 B2 6/2021 Suzuki et al.
11,065,428 B2 7/2021 Liu et al.
11,097,086 B2 8/2021 Liu et al.
11,103,259 B2 8/2021 Crichton et al.
11,147,954 B2 10/2021 Junger et al.
11,175,128 B2 11/2021 Junger et al.
11,179,553 B2 11/2021 Kendall et al.
11,186,633 B2 11/2021 Lee et al.
11,191,815 B2 12/2021 Gu et al.
11,202,895 B2 12/2021 Davis et al.
11,213,663 B2 1/2022 Baek et al.
11,230,469 B2 1/2022 Wang et al.
11,254,126 B2 2/2022 Wang et al.
11,266,822 B2 3/2022 Shimada
11,285,308 B2 3/2022 Kim et al.
11,291,816 B2 4/2022 Tadros et al.
11,318,292 B2 5/2022 Zvezdin et al.
11,369,314 B2 6/2022 Ledden
11,426,570 B2 8/2022 Nguyen et al.
11,452,853 B2 9/2022 Chen et al.
11,464,953 B2 10/2022 Han et al.
11,464,957 B2 10/2022 Lemaire
2004/0135118 A1 7/2004 Waggoner
2005/0137525 A1 6/2005 Wang et al.
2007/0078376 A1 4/2007 Smith
2007/0191761 A1 8/2007 Boone et al.

(56) References Cited

U.S. PATENT DOCUMENTS

2008/0039805 A1 2/2008 Frederickson et al.
2008/0108958 A1 5/2008 Carter et al.
2008/0245764 A1 10/2008 Pirk et al.
2008/0262416 A1 10/2008 Quan et al.
2008/0275400 A1 11/2008 Ferguson
2009/0131905 A1 5/2009 Allen et al.
2009/0171314 A1 7/2009 Ferguson
2009/0326415 A1 12/2009 Lim
2010/0030100 A1 2/2010 Tokumoto et al.
2010/0305473 A1* 12/2010 Yuzhakov ......... A61M 37/0015 604/173
2011/0014181 A1 1/2011 Thornton
2011/0152792 A1 6/2011 Takada
2011/0172609 A1 7/2011 Moga et al.
2012/0004626 A1 1/2012 Kuwahara et al.
2013/0006217 A1 1/2013 Hattersley et al.
2013/0085472 A1 4/2013 Shaari
2013/0218083 A1 8/2013 Yuzhakov
2013/0225956 A1 8/2013 Huang et al.
2013/0253446 A1 9/2013 Duan et al.
2014/0046292 A1 2/2014 Hattersley et al.
2014/0046293 A1 2/2014 Hattersley et al.
2014/0066842 A1 3/2014 Zhang et al.
2014/0066843 A1 3/2014 Zhang et al.
2014/0128811 A1 5/2014 Ferguson et al.
2014/0142492 A1 5/2014 Jung
2014/0296683 A1 10/2014 Cordero et al.
2014/0296780 A1 10/2014 Lyon et al.
2014/0371713 A1 12/2014 Quan et al.
2015/0030642 A1 1/2015 Wu et al.
2015/0202418 A1 7/2015 Simon et al.
2015/0290163 A1 10/2015 Quan et al.
2015/0352777 A1 12/2015 DeSimone et al.
2017/0189493 A1 7/2017 Hattersley et al.
2017/0189660 A1 7/2017 Baek
2017/0209367 A1* 7/2017 Zhang .................... A61K 38/47
2017/0209391 A1 7/2017 Shim et al.
2017/0209553 A1 7/2017 Kaspar et al.
2017/0296465 A1 10/2017 Yoshida et al.
2018/0015272 A1 1/2018 Kim
2018/0078498 A1 3/2018 Petersson et al.
2018/0140815 A1 5/2018 Ono et al.
2018/0161252 A1 6/2018 Francis et al.
2018/0193256 A1 7/2018 Kabata et al.
2018/0264244 A1 9/2018 Meliga et al.
2018/0271800 A1 9/2018 Liu et al.
2018/0304062 A1 10/2018 Falo, Jr. et al.
2018/0326195 A1 11/2018 Yamabe et al.
2018/0344631 A1 12/2018 Zhang et al.
2018/0344998 A1 12/2018 Ono
2018/0369136 A1 12/2018 Narayan et al.
2019/0001108 A1 1/2019 Ono
2019/0015650 A1 1/2019 Jaklenec et al.
2019/0022365 A1 1/2019 Chowdhury et al.
2019/0111188 A1 4/2019 Kabata et al.
2019/0184149 A1 6/2019 Yang et al.
2019/0216363 A1 7/2019 Holmes et al.
2019/0232034 A1 8/2019 Lee
2019/0290738 A1 9/2019 Hattersley et al.
2019/0344062 A1 11/2019 Quan et al.
2019/0351206 A1 11/2019 Gu et al.
2019/0374146 A1 12/2019 De Brouwer et al.
2019/0381299 A1 12/2019 De Brouwer et al.
2019/0388669 A1 12/2019 Martinez Canovas et al.
2019/0388670 A1 12/2019 De Brouwer et al.
2020/0009767 A1 1/2020 Li
2020/0015751 A9 1/2020 Chickering, III et al.
2020/0054869 A1 2/2020 Liu et al.
2020/0094033 A1 3/2020 De Brouwer et al.
2020/0121900 A1 4/2020 Kang et al.
2020/0129748 A1 4/2020 Lee et al.
2020/0164192 A1 5/2020 Quan et al.
2020/0170940 A1 6/2020 Quan et al.
2020/0171290 A1 6/2020 Henning et al.
2020/0188649 A1 6/2020 Henke et al.
2020/0197286 A1 6/2020 Shim et al.
2020/0206489 A1 7/2020 Ronnander et al.
2020/0215187 A1 7/2020 Takada
2020/0238065 A1 7/2020 Prausnitz et al.
2020/0246450 A1 8/2020 Junger et al.
2020/0324096 A1 10/2020 Hwang et al.
2020/0330016 A1 10/2020 Espina Perez et al.
2020/0368512 A1 11/2020 Burton
2020/0376247 A1 12/2020 Shimada et al.
2021/0052705 A1 2/2021 Hattersley et al.
2021/0060321 A1 3/2021 Amir
2021/0106800 A1 4/2021 Quan et al.
2021/0130467 A1 5/2021 Zalevsky et al.
2021/0146104 A1 5/2021 Quan et al.
2021/0170151 A1 6/2021 Chang
2021/0170154 A1 6/2021 Jung et al.
2021/0170643 A1 6/2021 Hwang et al.
2021/0244927 A1 8/2021 Yoshida et al.
2021/0317513 A1 10/2021 Mahmood et al.
2021/0322744 A1 10/2021 Burnier et al.
2021/0322745 A1 10/2021 Agarwal et al.
2021/0393543 A1 12/2021 Wu et al.
2022/0072289 A1 3/2022 Liu et al.
2022/0226626 A1 7/2022 Tadros et al.

FOREIGN PATENT DOCUMENTS

CN 102553066 B 7/2013
CN 103550191 A 2/2014
CN 104069585 A 10/2014
CN 104338235 A 2/2015
CN 104888343 A 9/2015
CN 105816952 A 8/2016
CN 106943134 A 7/2017
CN 107050635 A 8/2017
CN 107320841 A 11/2017
CN 108096699 A 6/2018
CN 108785244 A 11/2018
CN 108853709 A 11/2018
CN 109045459 A 12/2018
CN 109045460 A 12/2018
CN 109200012 A 1/2019
CN 109364017 A 2/2019
CN 110812687 A 2/2020
CN 110840822 A 2/2020
CN 110870846 A 3/2020
CN 110870943 A 3/2020
CN 111184942 A 5/2020
EP 2359885 A1 8/2011
EP 3520979 A1 8/2019
IN 201001832 P3 3/2011
IN 201303227 P4 7/2014
IN 201408455 P4 7/2016
IN 201617000958 A 7/2016
IN 202047009462 A 3/2020
JP 2009072271 A 4/2009
JP 2009273772 A 11/2009
JP 2010094414 A 4/2010
JP 4521492 B2 8/2010
JP 2011224308 A 11/2011
JP 2013111104 A 6/2013
JP 5472673 B2 4/2014
JP 5688752 B2 3/2015
JP 5778622 B2 9/2015
JP 2016067681 A 5/2016
JP 6121674 B2 4/2017
JP 2017145226 A 8/2017
JP 6198373 B2 9/2017
JP 6255759 B2 1/2018
JP 6269111 B2 1/2018
JP 2018196401 A 12/2018
JP 6533189 B2 6/2019
JP 6541128 B2 7/2019
JP 2019162438 A 9/2019
JP 2020097529 A 6/2020
KR 100792382 B1 1/2008
KR 2012024102 A 3/2012
KR 101373739 B1 3/2014
KR 101484161 B1 1/2015

(56) References Cited

FOREIGN PATENT DOCUMENTS

| | | | | |
|---|---|---|---|---|
| KR | 101491075 B1 | 2/2015 | | |
| KR | 101621945 B1 | 7/2015 | | |
| KR | 101574760 B1 | 12/2015 | | |
| KR | 101590613 B1 | 2/2016 | | |
| KR | 101629007 B1 | 6/2016 | | |
| KR | 20160128898 A | 11/2016 | | |
| KR | 20160145476 A | 12/2016 | | |
| KR | 20170000745 A | 1/2017 | | |
| KR | 101751953 B1 | 7/2017 | | |
| KR | 101779393 B1 | 9/2017 | | |
| KR | 101785766 B1 | 10/2017 | | |
| KR | 20170135773 A | 12/2017 | | |
| KR | 101832716 B1 | 2/2018 | | |
| KR | 20180052418 A | 5/2018 | | |
| KR | 20180079728 A | 7/2018 | | |
| KR | 1891398 B1 | 8/2018 | | |
| KR | 101924289 B1 | 11/2018 | | |
| KR | 101942172 B1 | 1/2019 | | |
| KR | 20190038433 A | 4/2019 | | |
| KR | 20190065003 A | 6/2019 | | |
| KR | 20190070335 A | 6/2019 | | |
| KR | 102006071 B1 | 7/2019 | | |
| KR | 20190080549 A | 7/2019 | | |
| KR | 20190088340 A | 7/2019 | | |
| KR | 20190091008 A | 8/2019 | | |
| KR | 20190103903 A | 9/2019 | | |
| KR | 102031062 B1 | 10/2019 | | |
| KR | 20190123642 A | 11/2019 | | |
| KR | 102093235 B1 | 3/2020 | | |
| KR | 102123508 B1 | 6/2020 | | |
| KR | 20200077469 A | 6/2020 | | |
| TW | I564035 | 1/2017 | | |
| WO | WO 1990/07348 A1 | 7/1990 | | |
| WO | WO 2000/016833 A1 | 3/2000 | | |
| WO | WO 2000/35530 A1 | 6/2000 | | |
| WO | WO 2001/066065 A2 | 9/2001 | | |
| WO | WO 2002/34017 A2 | 4/2002 | | |
| WO | WO-2004058851 A1 | * | 7/2004 | ............ C08G 63/80 |
| WO | WO 2010/140760 A2 | 12/2010 | | |
| WO | WO 2011/071287 A2 | 6/2011 | | |
| WO | WO 2012/128363 A1 | 9/2012 | | |
| WO | WO 2014/142749 A1 | 9/2014 | | |
| WO | WO 2015/149031 A1 | 9/2016 | | |
| WO | WO 2016/163752 A1 | 10/2016 | | |
| WO | WO 2017/018086 A1 | 2/2017 | | |
| WO | WO 2017/043627 A1 | 3/2017 | | |
| WO | WO 2017/131397 A1 | 8/2017 | | |
| WO | WO 2017/131398 A1 | 8/2017 | | |
| WO | WO 2017/155267 A1 | 9/2017 | | |
| WO | WO 2017/179613 A1 | 10/2017 | | |
| WO | WO 2017/179775 A1 | 10/2017 | | |
| WO | WO 2017/204418 A1 | 11/2017 | | |
| WO | WO 2018/044022 A1 | 3/2018 | | |
| WO | WO 2018/211421 A1 | 11/2018 | | |
| WO | WO 2018/226069 A1 | 12/2018 | | |
| WO | WO 2019/050121 A1 | 3/2019 | | |
| WO | WO 2019/058328 A1 | 3/2019 | | |
| WO | WO 2019/058329 A1 | 3/2019 | | |
| WO | WO 2019/082099 A1 | 5/2019 | | |
| WO | WO 2019/103404 A1 | 5/2019 | | |
| WO | WO 2019/136133 A1 | 7/2019 | | |
| WO | WO 2019/150308 A1 | 8/2019 | | |
| WO | WO 2019/186129 A1 | 10/2019 | | |
| WO | WO 2019/207528 A1 | 10/2019 | | |
| WO | WO 2019/225288 A1 | 11/2019 | | |
| WO | WO 2019/230990 A1 | 12/2019 | | |
| WO | WO 2020/004666 A1 | 1/2020 | | |
| WO | WO 2020/017441 A1 | 1/2020 | | |
| WO | WO 2020/041694 A1 | 2/2020 | | |
| WO | WO 2020/100854 A1 | 5/2020 | | |
| WO | WO 2020/138482 A1 | 7/2020 | | |
| WO | WO 2021/141297 A1 | 7/2021 | | |

OTHER PUBLICATIONS

"TTP Designs Commerical-Ready Applicator for 3M's Hollow Microneedle Array", 3M Science, Applied to Life, Aug. 11, 2020, 5 pages.

Allen, "Cancer Vaccine Tested in Novel Delivery System", Packaging Digest, Mar. 8, 2017, 5 pages.

Burton et al, "Rapid Intradermal Delivery of Liquid Formulations Using a Hollow Micostructured Array", Pharmaceutical Research, vol. 28, No. 1, 2011, 16 pages.

Controlled Release Society, $35^{th}$ Annual Meeting and Exposition of the Controlled Release Society, Jul. 12-16, 2008, New York, New York, United States, vol. 1, 50 pages.

Duan et al, "Enhanced Delivery of Topically-Applied Formulations Following Skin Pre-Treatment with a Hand-Applied, Plastic Microneedle Array", Current Drug Delivery, 2011, pp. 557-565.

Fuller et al, "Enhanced Immunogenicity of a Nanoparticle Therapeutic Cancer Vaccine Targeting HAAH Delivered Intradermally using 3M's Hollow Microstructed Transdermal System", Journal for Immuno Therapy of Cancer, vol. 2, 2015, 2 pages.

Hamilton, "Fabrication and Analysis of Injection Molded Plastic Microneedle Arrays", Georgia Institute of Technology, Graduate Thesis, 2011, 310 pages.

International Search Report and Written Opinion for Application No. PCT/US2021/028350, mailed on Aug. 9, 2021, 15 pages.

Nair, "Micro-Injection Moulded Microneedles for Drug Delivery", University of Bradford, PHD Thesis, 2014, 266 pages.

Sammoura et al, "Polymeric Microneedle Fabrication using a Microinjection Molding Technique", Microsystem Technologies, vol. 13, 2007, 6 pages.

Shetty, "Investigation of Geometrical Effects on Microneedle Geometry for Transdermal Applications", University of South Florida, Graduate Thesis, Jul. 19, 2005, 103 pages.

Campus® Datasheet on Vectra® MT® 1300—LCP from Celanese dated 2023, 3 pages.

Vectra® LCP Design Guide from Celanese dated Sep. 13, 2013, 80 pages.

Supplementary European Search Report dated Mar. 7, 2024, 16 pages.

* cited by examiner

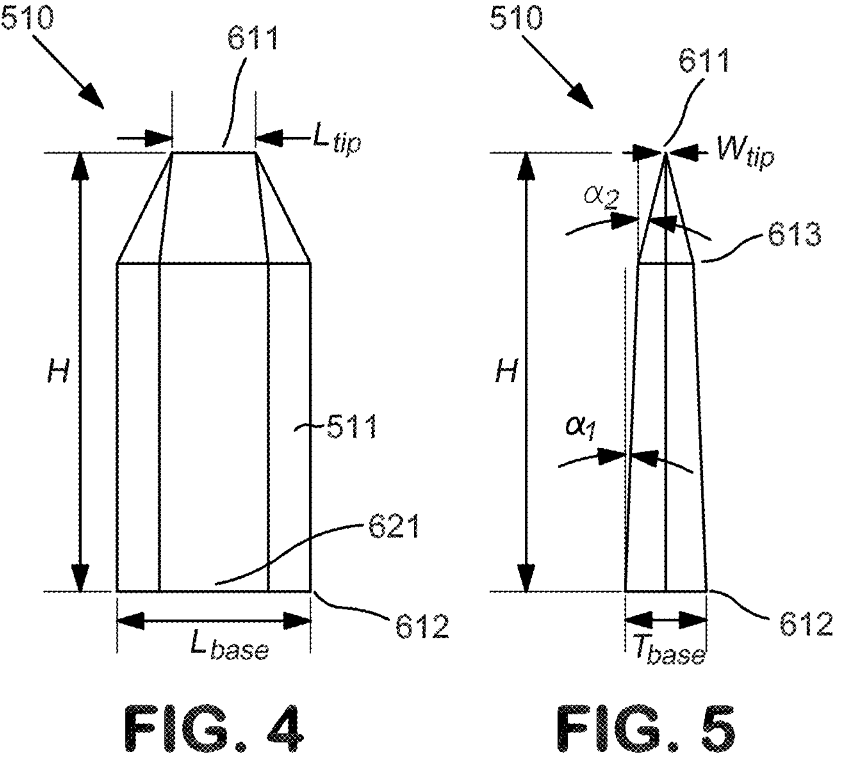
FIG. 4
FIG. 5
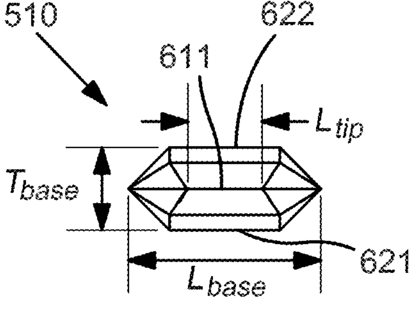
FIG. 6

MICRONEEDLE ASSEMBLY

CROSS REFERENCE TO RELATED APPLICATIONS

The present application claims filing benefit of U.S. Provisional Patent Application Ser. No. 63/016,560 having a filing date of Apr. 28, 2020 and U.S. Provisional Patent Application Ser. No. 63/034,429 having a filing date of Jun. 4, 2020, which are incorporated herein by reference in their entirety.

BACKGROUND OF THE INVENTION

Due to their relatively high molecular weight and viscosity, most vaccines require delivery to a subject through oral delivery, injections, or infusions. Unfortunately, these methods are problematic for a variety of reasons. For instance, injections often utilize small gauge needles that are painful and can require extremely high pressure over a long period of time for delivery of the vaccine. Oral delivery likewise requires successful absorption of the vaccine through the epithelial lining of the digestive tract and avoidance of breakdown by digestive materials. Both injection and oral delivery also tend to provide bursts of the vaccine and wide swings in system concentration, rather than a preferred steady-state delivery. Infusion therapy can also be used to deliver a vaccine directly to blood vessels, muscles, or subcutaneous connective tissue. However, infusion therapy is invasive, which increases the risk for infection at the infusion site and necessitates the use of pumps, transdermal tubing, etc. As a result of these issues, attempts have also been to deliver vaccines through transdermal delivery devices. Unfortunately, due to their relatively small size, it is often complex to manufacture microneedles of a consistent size and shape. Moreover, the microneedles are often not properly aligned with each other, which can cause inconsistent delivery of the vaccine dosage.

As such, a need currently exists for an improved transdermal delivery device.

SUMMARY OF THE INVENTION

In accordance with one embodiment of the present invention, a microneedle assembly is disclosed that comprises at least one microneedle extending outwardly from a support. The microneedle includes a polymer composition containing a thermoplastic polymer having a melting temperature of about 250° C. or more. The polymer composition exhibits a melt viscosity of about 100 Pa-s or less and a tensile elongation of about 5% or less.

Other features and aspects of the present invention are set forth in greater detail below.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which:

FIG. 4 is a schematic front view of one embodiment of a microneedle shown in the assembly of FIG. 2;

FIG. 5 is a schematic side view of one embodiment of a microneedle shown in the assembly of FIG. 2; and FIG. 6 is a schematic plan view of one embodiment of a microneedle shown in the assembly of FIG. 2.

DETAILED DESCRIPTION

Figure 1:
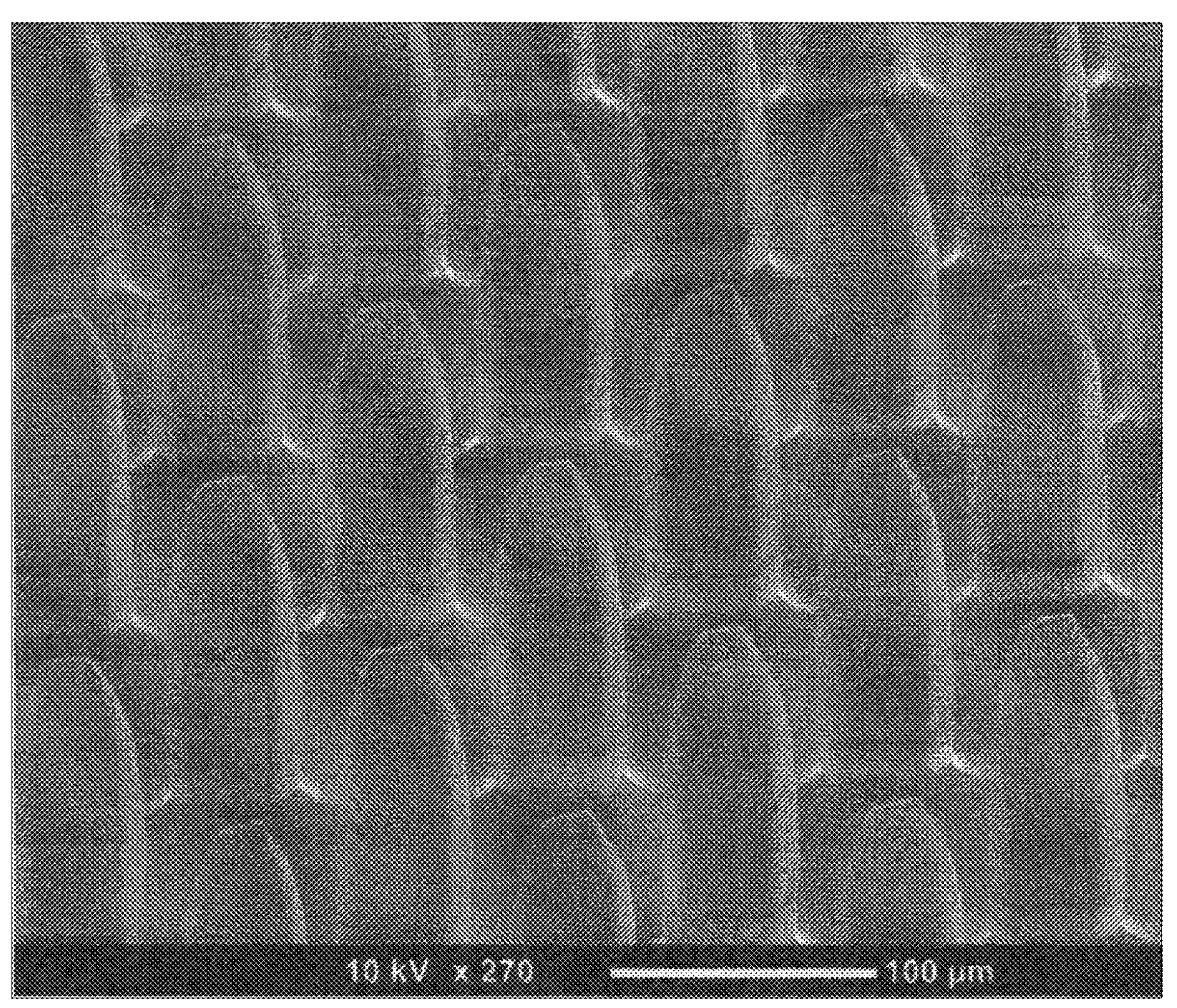
FIG. 1 is an SEM image of one embodiment of a microneedle assembly that may be formed in accordance with the present invention.

It is to be understood by one of ordinary skill in the art that the present discussion is a description of exemplary embodiments only, and is not intended as limiting the broader aspects of the present invention.

Generally speaking, the present invention is directed to a microneedle assembly that is capable of transdermal delivery of a drug compound, such as a vaccine, (e.g., vaccine) across a dermal barrier of a subject (e.g., human), and/or detecting the presence of an analyte in the subject. The microneedles may be formed from a thermoplastic polymer composition having a melt viscosity that is sufficiently low to enable it to be readily molded into the small dimensions required for a microneedle. For example, the polymer composition may have a melt viscosity of about 100 Pa-s or less, in some embodiments about 80 Pa-s or less, in some embodiments from about 1 Pa-s to about 60 Pa-s, and in some embodiments, from about 2 to about 50 Pa-s, as determined in accordance with ISO Test No. 11443:2014 at a shear rate at a shear rate of 1,000 seconds$^{-1}$ at a temperature of about 30° C. above the melting temperature (e.g., about 380° C.). The polymer composition may also have a melt viscosity of from about 150 Pa-s or less, in some embodiments about 100 Pa-s or less, in some embodiments from about 5 Pa-s to about 90 Pa-s, and in some embodiments, from about 10 to about 70 Pa-s, as determined in accordance with ISO Test No. 11443:2014 at a shear rate at a shear rate of 400 seconds$^{-1}$ at a temperature of about 30° C. above the melting temperature (e.g., about 380° C.).

Conventionally, it was believed that thermoplastic polymer compositions exhibiting such a low melt viscosity would not also possess sufficiently good thermal and mechanical properties to enable good physical integrity for use in forming microneedles that are in substantial alignment and have a consistent shape and size. Contrary to conventional thought, however, the present inventors have discovered through careful control of the particular thermoplastic polymer(s) and/or other optional material employed, the resulting polymer composition can also possess both excellent thermal and mechanical properties. More particularly, the polymer composition contains a thermoplastic polymer has a melting temperature of about 250° C. or more, in some embodiments about 275° C. or more, in some embodiments about 300° C. or more, and in some embodiments, from about 320° C. to about 450° C., such as determined in accordance with ISO 11357-2:2013. Even at such melting temperatures, the ratio of the deflection temperature under load ("DTUL"), a measure of short-term heat resistance, to the melting temperature may still remain relatively high, which can, among other things, allow the use of high-speed processes for forming the microneedles. For example, the ratio may range from about 0.5 to about 1.00, in some embodiments from about 0.65 to about 0.95, and in some embodiments from about 0.75 to about 0.85. The specific DTUL values may, for instance, be about 160° C. or more, in some embodiments from about 200° C. to about 350° C., in some embodiments from about 220° C. to about 320° C., and in some embodiments from about 250° C. to about 300° C., such as determined in accordance with ISO Test No. 75-2:2013 (technically equivalent to ASTM D648-07) at a load of 1.8 Megapascals.

The polymer composition may be generally stiff in nature so that it is capable of maintaining the desired degree of physical integrity during formation of the microneedles. Such stiffness may be generally characterized by a low tensile elongation and/or a high tensile modulus. For example, the tensile elongation may be about 5% or less, in some embodiments about 4% or less, in some embodiments, from about 0.1 to about 3.5%, in some embodiments from about 0.2% to about 3%, and in some embodiments, from about 0.5% to about 2.5%, such as determined in accordance with ISO Test No. 527:2012 at a temperature of about 23° C. The tensile modulus may likewise be about 7,000 MPa or more, in some embodiments about 7,500 MPa or more, in some embodiments from about 8,000 MPa to about 25,000 MPa, in some embodiments about 8,500 MPa to about 20,000 MPa, and in some embodiments from about 9,000 MPa to about 15,000 MPa, such as determined in accordance with ISO Test No. 527:2012 at a temperature of about 23° C. The polymer composition may also exhibit other good mechanical properties. For example, the polymer composition may exhibit a tensile strength of about 10 MPa or more, in some embodiments about 50 MPa or more, in some embodiments from about 70 MPa to about 300 MPa, and in some embodiments from about 80 MPa to about 200 MPa, such as determined in accordance with ISO Test No. 527:2012 at a temperature of about 23° C.

The polymer composition may also exhibit a flexural strength of from about 40 to about 500 MPa, in some embodiments from about 50 to about 300 MPa, and in some embodiments, from about 100 to about 200 MPa; flexural break strain of from about 0.5% to about 15%, in some embodiments from about 0.6% to about 10%, and in some embodiments, from about 1% to about 5%; and/or flexural modulus of from about 5,000 MPa to about 20,000 MPa, in some embodiments, from about 6,000 MPa to about 15,000 MPa, and in some embodiments, from about 8,000 MPa to about 12,000 MPa. The flexural properties may be determined in accordance with ISO Test No. 178:2010 (technically equivalent to ASTM D790-10) at 23° C. The composition may also exhibit a Charpy unnotched and/or notched impact strength of about 1 $kJ/m^2$ or more, in some embodiments from about 1.5 to about 30 $kJ/m^2$, and in some embodiments, from about 2 to about 20 $kJ/m^2$, measured at 23° C. according to ISO Test No. 179-1:2010 (technically equivalent to ASTM D256-10e1).

Various embodiments of the present invention will now be described in more detail.

I. Polymer Composition

A. Thermoplastic Polymer

Any of a variety of thermoplastic polymers having the characteristics noted above may be employed in the polymer composition. Particularly examples of such polymers may include, for instance, wholly or partially aromatic polymers, such as polyarylene sulfides (e.g., polyphenylene sulfide), polyamides (e.g., aromatic polyamides or semi-aromatic polyamides), polyaryleneketones (e.g., polyetheretherketone), liquid crystalline polymers, etc., as well as aliphatic polymers, such as aliphiatic polyamides.

Aromatic polymers are particularly suitable for use in the polymer composition. The aromatic polymer can be semi-crystalline or crystalline in nature. One example of a suitable semi-crystalline aromatic polymer, for instance, is an aromatic polyamide. Aromatic polyamides typically contain repeating units held together by amide linkages (NH—CO) and are synthesized through the polycondensation of dicarboxylic acids (e.g., aromatic dicarboxylic acids), diamines (e.g., aliphatic diamines), etc. For example, the aromatic polyamide may contain aromatic repeating units derived from an aromatic dicarboxylic acid, such as terephthalic acid, isophthalic acid, 2,6-naphthalenedicarboxylic acid, 2,7-naphthalenedicarboxylic acid, 1,4-naphthalenedicarboxylic acid, 1,4-phenylenedioxy-diacetic acid, 1,3-phenylenedioxy-diacetic acid, diphenic acid, 4,4'-oxydibenzoic acid, diphenylmethane-4,4'-dicarboxylic acid, diphenylsulfone-4,4'-dicarboxylic acid, 4,4'-biphenyldicarboxylic acid, etc., as well as combinations thereof. Terephthalic acid is particularly suitable. Of course, it should also be understood that other types of acid units may also be employed, such as aliphatic dicarboxylic acid units, polyfunctional carboxylic acid units, etc. The aromatic polyamide may also contain aliphatic repeating units derived from an aliphatic diamine, which typically has from 4 to 14 carbon atoms. Examples of such diamines include linear aliphatic alkylenediamines, such as 1,4-tetramethylenediamine, 1,6-hexanediamine, 1,7-heptanediamine, 1,8-octanediamine, 1,9-nonanediamine, 1,10-decanediamine, 1,11-undecanediamine, 1,12-dodecanediamine, etc.; branched aliphatic alkylenediamines, such as 2-methyl-1,5-pentanediamine, 3-methyl-1,5 pentanediamine, 2,2,4-trimethyl-1,6-hexanediamine, 2,4,4-trimethyl-1,6-hexanediamine, 2,4-dimethyl-1,6-hexanediamine, 2-methyl-1,8-octanediamine, 5-methyl-1,9-nonanediamine, etc.; as well as combinations thereof. Repeating units derived from 1,9-nonanediamine and/or 2-methyl-1,8-octanediamine are particularly suitable. Of course, other diamine units may also be employed, such as alicyclic diamines, aromatic diamines, etc.

Particularly suitable aromatic polyamides may include poly(nonamethylene terephthalamide) (PA9T), poly(nonamethylene terephthalamide/nonamethylene decanediamide) (PA9T/910), poly(nonamethylene terephthalamide/nonamethylene dodecanediamide) (PA9T/912), poly(nonamethylene terephthalamide/11-aminoundecanamide) (PA9T/11), poly(nonamethylene terephthalamide/12-aminododecanamide) (PA9T/12), poly(decamethylene terephthalamide/11-aminoundecanamide) (PA10T/11), poly(decamethylene terephthalamide/12-aminododecanamide) (PA10T/12), poly (decamethylene terephthalamide/decamethylene decanediamide) (PA10T/1010), poly(decamethylene terephthalamide/decamethylene dodecanediamide) (PA10T/1012), poly(decamethylene terephlhalamide/tetramethylene hexanediamide) (PA10T/46), poly(decamethylene terephthalamide/caprolactam) (PA10T/6), poly(decamethylene terephthalamide/hexamethylene hexanediamide) (PA10T/66), poly(dodecamethylene lerephthalamide/dodecamelhylene dodecanediarnide) (PA12T/1212), poly(dodecamethylene terephthalamide/caprolactam) (PA12T/6), poly (dodecamethylene terephthalamide/hexamethylene hexanediamide) (PA12T/66), and so forth. Yet other examples of suitable aromatic polyamides are described in U.S. Pat. No. 8,324,307 to Harder, et al.

Another suitable semi-crystalline aromatic polymer that may be employed in the present invention is a polyaryletherketone. Particularly suitable polyaryletherketones are those that primarily include phenyl moieties in conjunction with ketone and/or ether moieties. Examples of such polymers include polyetheretherketone ("PEEK"), polyetherketone ("PEK"), polyetherketoneketone ("PEKK"), polyetherketoneetherketoneketone ("PEKEKK"), polyetheretherketoneketone ("PEEKK"), polyether-diphenyl-etherether-diphenyl-ether-phenyl-ketone-phenyl, etc., as well as blends and copolymers thereof.

In addition to the polymers referenced above, crystalline polymers may also be employed in the polymer composition. Particularly suitable thermoplastic polymers for use in the polymer composition are liquid crystalline polymers. Liquid crystalline polymers are generally classified as "thermotropic" to the extent that they can possess a rod-like structure and exhibit a crystalline behavior in their molten state (e.g., thermotropic nematic state). Such polymers may be formed from one or more types of repeating units as is known in the art. A liquid crystalline polymer may, for example, contain one or more aromatic ester repeating units generally represented by the following Formula (I):

(I)

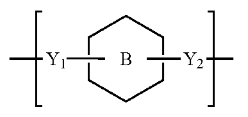

wherein, ring B is a substituted or unsubstituted 6-membered aryl group (e.g., 1,4-phenylene or 1,3-phenylene), a substituted or unsubstituted 6-membered aryl group fused to a substituted or unsubstituted 5- or 6-membered aryl group (e.g., 2,6-naphthalene), or a substituted or unsubstituted 6-membered aryl group linked to a substituted or unsubstituted 5- or 6-membered aryl group (e.g., 4,4-biphenylene); and $Y_1$ and $Y_2$ are independently O, C(O), NH, C(O)HN, or NHC(O).

Typically, at least one of $Y_1$ and $Y_2$ are C(O). Examples of such aromatic ester repeating units may include, for instance, aromatic dicarboxylic repeating units ($Y_1$ and $Y_2$ in Formula I are C(O)), aromatic hydroxycarboxylic repeating units ($Y_1$ is O and $Y_2$ is C(O) in Formula I), as well as various combinations thereof.

Aromatic hydroxycarboxylic repeating units, for instance, may be employed that are derived from aromatic hydroxycarboxylic acids, such as, 4-hydroxybenzoic acid; 4-hydroxy-4'-biphenylcarboxylic acid; 2-hydroxy-6-naphthoic acid; 2-hydroxy-5-naphthoic acid; 3-hydroxy-2-naphthoic acid; 2-hydroxy-3-naphthoic acid; 4'-hydroxyphenyl-4-benzoic acid; 3'-hydroxyphenyl-4-benzoic acid; 4'-hydroxyphenyl-3-benzoic acid, etc., as well as alkyl, alkoxy, aryl and halogen substituents thereof, and combination thereof. Particularly suitable aromatic hydroxycarboxylic acids are 4-hydroxybenzoic acid ("HBA") and 6-hydroxy-2-naphthoic acid ("HNA"). When employed, repeating units derived from hydroxycarboxylic acids (e.g., HBA and/or HNA) typically constitute about 20 mol. % or more, in some embodiments about 25 mol. % or more, in some embodiments about 30 mol. % or more, in some embodiments about 40 mol. % or more, in some embodiments about 50 mole % or more, in some embodiments from about 55 mol. % to 100 mol. %, and in some embodiments, from about 60 mol. % to about 95 mol. % of the polymer.

Aromatic dicarboxylic repeating units may also be employed that are derived from aromatic dicarboxylic acids, such as terephthalic acid, isophthalic acid, 2,6-naphthalenedicarboxylic acid, diphenyl ether-4,4'-dicarboxylic acid, 1,6-naphthalenedicarboxylic acid, 2,7-naphthalenedicarboxylic acid, 4,4'-dicarboxybiphenyl, bis(4-carboxyphenyl) ether, bis(4-carboxyphenyl)butane, bis(4-carboxyphenyl) ethane, bis(3-carboxyphenyl)ether, bis(3-carboxyphenyl) ethane, etc., as well as alkyl, alkoxy, aryl and halogen substituents thereof, and combinations thereof. Particularly suitable aromatic dicarboxylic acids may include, for instance, terephthalic acid ("TA"), isophthalic acid ("IA"), and 2,6-naphthalenedicarboxylic acid ("NDA"). When employed, repeating units derived from aromatic dicarboxylic acids (e.g., IA, TA, and/or NDA) each typically constitute from about 1 mol. % to about 40 mol. %, in some embodiments from about 2 mol. % to about 30 mol. %, and in some embodiments, from about 5 mol. % to about 25% of the polymer.

Other repeating units may also be employed in the polymer. In certain embodiments, for instance, repeating units may be employed that are derived from aromatic diols, such as hydroquinone, resorcinol, 2,6-dihydroxynaphthalene, 2,7-dihydroxynaphthalene, 1,6-dihydroxynaphthalene, 4,4'-dihydroxybiphenyl (or 4,4'-biphenol), 3,3'-dihydroxybiphenyl, 3,4'-dihydroxybiphenyl, 4,4'-dihydroxybiphenyl ether, bis(4-hydroxyphenyl)ethane, etc., as well as alkyl, alkoxy, aryl and halogen substituents thereof, and combinations thereof. Particularly suitable aromatic diols may include, for instance, hydroquinone ("HQ") and 4,4'-biphenol ("BP"). When employed, repeating units derived from aromatic diols (e.g., HQ and/or BP) typically constitute from about about 1 mol. % to about 50 mol. %, in some embodiments from about 1 to about 40 mol. %, in some embodiments from about 2 mol. % to about 40 mol. %, in some embodiments from about 5 mol. % to about 35 mol. %, and in some embodiments, from about 5 mol. % to about 25% of the polymer.

Repeating units may also be employed, such as those derived from aromatic amides (e.g., acetaminophen ("APAP")) and/or aromatic amines (e.g., 4-aminophenol ("AP"), 3-aminophenol, 1,4-phenylenediamine, 1,3-phenylenediamine, etc.). When employed, repeating units derived from aromatic amides (e.g., APAP) and/or aromatic amines (e.g., AP) typically constitute from about 0.1 mol. % to about 20 mol. %, in some embodiments from about 0.5 mol. % to about 15 mol. %, and in some embodiments, from about 1 mol. % to about 10% of the polymer. It should also be understood that various other monomeric repeating units may be incorporated into the polymer. For instance, in certain embodiments, the polymer may contain one or more repeating units derived from non-aromatic monomers, such as aliphatic or cycloaliphatic hydroxycarboxylic acids, dicarboxylic acids, diols, amides, amines, etc. Of course, in other embodiments, the polymer may be "wholly aromatic" in that it lacks repeating units derived from non-aromatic (e.g., aliphatic or cycloaliphatic) monomers.

In certain embodiments, the liquid crystalline polymer may be a "high naphthenic" polymer to the extent that it contains a relatively high content of repeating units derived from naphthenic hydroxycarboxylic acids and naphthenic dicarboxylic acids, such as NDA, HNA, or combinations thereof. That is, the total amount of repeating units derived from naphthenic hydroxycarboxylic and/or dicarboxylic acids (e.g., NDA, HNA, or a combination of HNA and NDA) is typically about 10 mol. % or more, in some embodiments about 12 mol. % or more, in some embodiments about 15 mol. % or more, in some embodiments about 18 mol. % or more, in some embodiments about 30 mol. % or more, in some embodiments about 40 mol. % or more, in some embodiments about 45 mol. % or more, in some embodiments 50 mol. % or more, in some embodiments about 55 mol. % or more, and in some embodiments, from about 55 mol. % to about 95 mol. % of the polymer. Without intending to be limited by theory, it is believed that such "high naphthenic" polymers are capable of reducing the tendency of the polymer composition to absorb water, which can aid in processability and proper alignment of the microneedles. Namely, such high naphthenic polymers typically have a water adsorption of about 0.015% or less, in some embodiments about 0.01% or less, and in some embodiments, from about 0.0001% to about 0.008% after being immersed in water for 24 hours in accordance with ISO 62-1:2008. The high naphthenic polymers may also have a moisture adsorption of about 0.01% or less, in some embodiments about 0.008% or less, and in some embodiments, from about 0.0001% to about 0.006% after being exposed to a humid atmosphere (50% relative humidity) at a temperature of 23° C. in accordance with ISO 62-4:2008.

In one embodiment, for instance, the repeating units derived from HNA may constitute 30 mol. % or more, in some embodiments about 40 mol. % or more, in some embodiments about 45 mol. % or more, in some embodiments 50 mol. % or more, in some embodiments about 55 mol. % or more, and in some embodiments, from about 55 mol. % to about 95 mol. % of the polymer. In such embodiments, the liquid crystalline polymer may contain various other monomers, such as aromatic hydroxycarboxylic acid(s) (e.g., HBA) in an amount of from about 1 mol. % to about 50 mol. %, and in some embodiments from about 1 mol. % to about 20 mol. %, and in some embodiments, from about 2 mol. % to about 10 mol. %; aromatic dicarboxylic acid(s) (e.g., IA and/or TA) in an amount of from about 1 mol. % to about 40 mol. %, and in some embodiments, from about 5 mol. % to about 25 mol. %; and/or aromatic diol(s) (e.g., BP and/or HQ) in an amount of from about 1 mol. % to about 40 mol. %, and in some embodiments, from about 5 mol. % to about 25 mol. %. In another embodiment, the repeating units derived from NDA may constitute 10 mol. % or more, in some embodiments about 12 mol. % or more, in some embodiments about 15 mol. % or more, and in some embodiments, from about 18 mol. % to about 95 mol. % of the polymer. In such embodiments, the liquid crystalline polymer may also contain various other monomers, such as aromatic hydroxycarboxylic acid(s) (e.g., HBA) in an amount of from about 20 mol. % to about 60 mol. %, and in some embodiments, from about 30 mol. % to about 50 mol. %; aromatic dicarboxylic acid(s) (e.g., IA and/or TA) in an amount of from about 2 mol. % to about 30 mol. %, and in some embodiments, from about 5 mol. % to about 25 mol. %; and/or aromatic diol(s) (e.g., BP and/or HQ) in an amount of from about 2 mol. % to about 40 mol. %, and in some embodiments, from about 5 mol. % to about 35 mol. %.

Of course, "low naphthenic" liquid crystalline polymers may also be employed in the composition, either alone or in combination with "high naphthenic" liquid crystalline polymers. In such low naphthenic polymers, the total amount of repeating units derived from naphthenic hydroxycarboxylic and/or dicarboxylic acids (e.g., NDA, HNA, or a combination of HNA and NDA) is typically less than 10 mol. %, in some embodiments about 8 mol. % or less, in some embodiments about 6 mol. % or less, and in some embodiments, from about 1 mol. % to about 5 mol. % of the polymer.

Regardless of the particular constituents and nature of the polymer, the liquid crystalline polymer may be prepared by initially introducing the aromatic monomer(s) used to form the ester repeating units (e.g., aromatic hydroxycarboxylic acid, aromatic dicarboxylic acid, etc.) and/or other repeating units (e.g., aromatic diol, aromatic amide, aromatic amine, etc.) into a reactor vessel to initiate a polycondensation reaction. The particular conditions and steps employed in such reactions are well known, and may be described in more detail in U.S. Pat. No. 4,161,470 to Calundann; U.S. Pat. No. 5,616,680 to Linstid, III, et al.; U.S. Pat. No. 6,114,492 to Linstid, III, et al.; U.S. Pat. No. 6,514,611 to Shepherd, et al.; and WO 2004/058851 to Waggoner. The vessel employed for the reaction is not especially limited, although it is typically desired to employ one that is commonly used in reactions of high viscosity fluids. Examples of such a reaction vessel may include a stirring tank-type apparatus that has an agitator with a variably-shaped stirring blade, such as an anchor type, multistage type, spiral-ribbon type, screw shaft type, etc., or a modified shape thereof. Further examples of such a reaction vessel may include a mixing apparatus commonly used in resin kneading, such as a kneader, a roll mill, a Banbury mixer, etc.

If desired, the reaction may proceed through the acetylation of the monomers as known the art. This may be accomplished by adding an acetylating agent (e.g., acetic anhydride) to the monomers. Acetylation is generally initiated at temperatures of about 90° C. During the initial stage of the acetylation, reflux may be employed to maintain vapor phase temperature below the point at which acetic acid byproduct and anhydride begin to distill. Temperatures during acetylation typically range from between 90° C. to 150° C., and in some embodiments, from about 110° C. to about 150° C. If reflux is used, the vapor phase temperature typically exceeds the boiling point of acetic acid, but remains low enough to retain residual acetic anhydride. For example, acetic anhydride vaporizes at temperatures of about 140° C. Thus, providing the reactor with a vapor phase reflux at a temperature of from about 110° C. to about 130° C. is particularly desirable. To ensure substantially complete reaction, an excess amount of acetic anhydride may be employed. The amount of excess anhydride will vary depending upon the particular acetylation conditions employed, including the presence or absence of reflux. The use of an excess of from about 1 to about 10 mole percent of acetic anhydride, based on the total moles of reactant hydroxyl groups present is not uncommon.

Acetylation may occur in in a separate reactor vessel, or it may occur in situ within the polymerization reactor vessel. When separate reactor vessels are employed, one or more of the monomers may be introduced to the acetylation reactor and subsequently transferred to the polymerization reactor. Likewise, one or more of the monomers may also be directly introduced to the reactor vessel without undergoing pre-acetylation.

In addition to the monomers and optional acetylating agents, other components may also be included within the reaction mixture to help facilitate polymerization. For instance, a catalyst may be optionally employed, such as metal salt catalysts (e.g., magnesium acetate, tin(I) acetate, tetrabutyl titanate, lead acetate, sodium acetate, potassium acetate, etc.) and organic compound catalysts (e.g., N-methylimidazole). Such catalysts are typically used in amounts of from about 50 to about 500 parts per million based on the total weight of the recurring unit precursors. When separate reactors are employed, it is typically desired to apply the catalyst to the acetylation reactor rather than the polymerization reactor, although this is by no means a requirement.

The reaction mixture is generally heated to an elevated temperature within the polymerization reactor vessel to initiate melt polycondensation of the reactants. Polycondensation may occur, for instance, within a temperature range of from about 250° C. to about 380° C., and in some embodiments, from about 280° C. to about 380° C. For instance, one suitable technique for forming the aromatic polyester may include charging precursor monomers and acetic anhydride into the reactor, heating the mixture to a temperature of from about 90° C. to about 150° C. to acetylize a hydroxyl group of the monomers (e.g., forming acetoxy), and then increasing the temperature to from about 280° C. to about 380° C. to carry out melt polycondensation. As the final polymerization temperatures are approached, volatile byproducts of the reaction (e.g., acetic acid) may also be removed so that the desired molecular weight may be readily achieved. The reaction mixture is generally subjected to agitation during polymerization to ensure good heat and mass transfer, and in turn, good material homogeneity. The rotational velocity of the agitator may vary during the course of the reaction, but typically ranges from about 10 to about 100 revolutions per minute ("rpm"), and in some embodiments, from about 20 to about 80 rpm. To build molecular weight in the melt, the polymerization reaction may also be conducted under vacuum, the application of which facilitates the removal of volatiles formed during the final stages of polycondensation. The vacuum may be created by the application of a suctional pressure, such as within the range of from about 5 to about 30 pounds per square inch ("psi"), and in some embodiments, from about 10 to about 20 psi.

Following melt polymerization, the molten polymer may be discharged from the reactor, typically through an extrusion orifice fitted with a die of desired configuration, cooled, and collected. Commonly, the melt is discharged through a perforated die to form strands that are taken up in a water bath, pelletized and dried. In some embodiments, the melt polymerized polymer may also be subjected to a subsequent solid-state polymerization method to further increase its molecular weight. Solid-state polymerization may be conducted in the presence of a gas (e.g., air, inert gas, etc.). Suitable inert gases may include, for instance, include nitrogen, helium, argon, neon, krypton, xenon, etc., as well as combinations thereof. The solid-state polymerization reactor vessel can be of virtually any design that will allow the polymer to be maintained at the desired solid-state polymerization temperature for the desired residence time. Examples of such vessels can be those that have a fixed bed, static bed, moving bed, fluidized bed, etc. The temperature at which solid-state polymerization is performed may vary, but is typically within a range of from about 250° C. to about 350° C. The polymerization time will of course vary based on the temperature and target molecular weight. In most cases, however, the solid-state polymerization time will be from about 2 to about 12 hours, and in some embodiments, from about 4 to about 10 hours.

B. Other Additives

In some cases, the thermoplastic polymers may constitute the entire polymer composition (e.g., 100 wt. %). Nevertheless, it may be desirable in certain embodiments to include one or more additives within the polymer composition to help achieve the target properties. In such embodiments, the polymer composition typically contains one or more thermoplastic polymers (e.g., liquid crystalline polymers) in an amount of from about 30 wt. % to about 99 wt. %, in some embodiments from about 40 wt. % to about 95 wt. %, and in some embodiments, from about 50 wt. % to about 90 wt. % of the entire polymer composition, as well as one or more additives in an amount of from about 1 wt. % to about 70 wt. %, in some embodiments from about 5 wt. % to about 60 wt. %, and in some embodiments, from about 10 wt. % to about 50 wt. % of the polymer composition.

When employed, the particular nature of the additives may vary. For example, the polymer composition may contain a mineral filler, which may be in the form of particles (e.g., platelet-shaped, flake-shaped, etc.), fibers, and so forth. In one embodiment, for example, the mineral filler may include a particulate mineral filler, such as talc, halloysite, kaolinite, illite, montmorillonite, vermiculite, palygorskite, pyrophyllite, mica, diatomaceous earth, etc., as well as combinations thereof. Mica and/or talc may be particularly suitable. When employed, the present inventors have discovered that particulate mineral fillers of a relatively small size better aid in filling of a mold cavity, as well as ensuring proper microneedle alignment. In one particular embodiment, for example, the particulate mineral filler (e.g., talc) may have a median size (e.g., D50 size) of about 10 micrometers or less, in some embodiments from about 0.1 to about 8 micrometers, in some embodiments from about 0.5 to about 5 micrometers, and in some embodiments, from about 0.6 to about 2.5 micrometers. Besides silicates, other suitable mineral filler particles may include carbonates, such as calcium carbonate ($CaCO_3$) or a copper carbonate hydroxide ($Cu_2CO_3(OH)_2$), fluorides, such as calcium fluoride ($CaFl_2$); phosphates, such as calcium pyrophosphate ($Ca_2P_2O_7$), anhydrous dicalcium phosphate ($CaHPO_4$), or hydrated aluminum phosphate ($AlPO_4 \cdot 2H_2O$), glass (e.g., glass powder); etc. Mineral fibers (also known as "whiskers") may also be employed as a mineral filler in the polymer composition. Examples of such mineral fibers include those that are derived from silicates, such as neosilicates, sorosilicates, inosilicates (e.g., calcium inosilicates, such as wollastonite; calcium magnesium inosilicates, such as tremolite; calcium magnesium iron inosilicates, such as actinolite; magnesium iron inosilicates, such as anthophyllite; etc.), phyllosilicates (e.g., aluminum phyllosilicates, such as palygorskite), tectosilicates, etc.; sulfates, such as calcium sulfates (e.g., dehydrated or anhydrous gypsum); mineral wools (e.g., rock or slag wool); glass; and so forth. Particularly suitable are inosilicates, such as wollastonite fibers available from Nyco Minerals under the trade designation NYGLOS® (e.g., NYGLOS® 4W, NYGLOS® 5, or NYGLOS® 8). In addition to possessing the size characteristics noted above, the mineral fibers may also have a relatively high aspect ratio (average length divided by median width) to help further improve the mechanical properties. For example, the mineral fibers may have an aspect ratio of from about 1 to about 50, in some embodiments from about 2 to about 20, and in some embodiments, from about 4 to about 15. The volume average length of such mineral fibers may, for example, range from about 1 to about 200 micrometers, in some embodiments from about 2 to about 150 micrometers, in some embodiments from about 5 to about 100 micrometers, and in some embodiments, from about 10 to about 50 micrometers.

If desired, a tribological additive material may also be employed in the polymer composition to help achieve a good combination of low friction and good wear resistance for use in the microneedle assembly. In one embodiment, for instance, the tribological additive material may include a fluorinated additive. Without intending to be limited by theory, it is believed that the fluorinated additive can, among other things, improve the processing of the composition, such as by providing better mold filling, internal lubrication, mold release, etc. In certain embodiments, the fluorinated additive may include a fluoropolymer, which contains a hydrocarbon backbone polymer in which some or all of the hydrogen atoms are substituted with fluorine atoms. The backbone polymer may polyolefinic and formed from fluorine-substituted, unsaturated olefin monomers. The fluoropolymer can be a homopolymer of such fluorine-substituted monomers or a copolymer of fluorine-substituted monomers or mixtures of fluorine-substituted monomers and non-fluorine-substituted monomers. Along with fluorine atoms, the fluoropolymer can also be substituted with other halogen atoms, such as chlorine and bromine atoms. Representative monomers suitable for forming fluoropolymers for use in this invention are tetrafluoroethylene, vinylidene fluoride, hexafluoropropylene, chlorotrifluoroethylene, perfluoroethylvinyl ether, perfluoromethylvinyl ether, perfluoropropylvinyl ether, etc., as well as mixtures thereof. Specific examples of suitable fluoropolymers include polytetrafluoroethylene, perfluoroalkylvinyl ether, poly(tetrafluoroethylene-co-perfluoroalkyvinylether), fluorinated ethylene-propylene copolymer, ethylene-tetrafluoroethylene copolymer, polyvinylidene fluoride, polychlorotrifluoroethylene, etc., as well as mixtures thereof. The fluorinated additive may contain only the fluoropolymer, or it may also include other ingredients, such as those that aid in its ability to be uniformly dispersed within the polymer composition. In one embodiment, for example, the fluorinated additive may include a fluoropolymer in combination with a plurality of carrier particles. In such embodiments, for instance, the fluoropolymer may be coated onto the carrier particles. Silicate particles are particularly suitable for this purpose, such as talc, halloysite, kaolinite, illite, montmorillonite, vermiculite, palygorskite, pyrophyllite, calcium silicate, aluminum silicate, mica, diatomaceous earth, wollastonite, and so forth. Mica, for instance, may be a particularly suitable mineral for use in the present invention. The carrier particles may have an average particle size of from about 5 to about 50 micrometers, and in some embodiments, from about 10 to 20 micrometers. If desired, the carrier particles may also be in the shape of plate-like particles in that the ratio of its major axis to thickness is 2 or more.

A wide variety of other additional additives can also be included in the polymer composition, such as lubricants, fibrous fillers (e.g., glass fibers), thermally conductive fillers, pigments, antioxidants, stabilizers, surfactants, waxes, flame retardants, anti-drip additives, nucleating agents (e.g., boron nitride), flow modifiers, coupling agents, antimicrobials, pigments or other colorants, impact modifiers, and other materials added to enhance properties and processability.

II. Formation

The components used to form the polymer composition may be combined together using any of a variety of different techniques as is known in the art. In one particular embodiment, for example, the thermoplastic polymer and other optional additives are melt processed as a mixture within an extruder to form the polymer composition. The mixture may be melt-kneaded in a single-screw or multi-screw extruder at a temperature of from about 200° C. to about 450° C. In one embodiment, the mixture may be melt processed in an extruder that includes multiple temperature zones. The temperature of individual zones is typically set within about −60° C. to about 25° C. relative to the melting temperature of the polymer. By way of example, the mixture may be melt processed using a twin screw extruder such as a Leistritz 18-mm co-rotating fully intermeshing twin screw extruder. A general purpose screw design can be used to melt process the mixture. In one embodiment, the mixture including all of the components may be fed to the feed throat in the first barrel by means of a volumetric feeder. In another embodiment, different components may be added at different addition points in the extruder, as is known. For example, the polymer may be applied at the feed throat, and certain additives (e.g., particulate filler) may be supplied at the same or different temperature zone located downstream therefrom. Regardless, the resulting mixture can be melted and mixed then extruded through a die. The extruded polymer composition can then be quenched in a water bath to solidify and granulated in a pelletizer followed by drying.

III. Microneedle Assembly

The microneedle assembly typically includes one or more microneedles that extend outwardly from a support. Any of a variety of techniques may be employed to form the microneedles, such as embossing (e.g., hot embossing, roll-to-roll molding, etc.); molding, such as micro-molding, injection molding (e.g. low-pressure injection molding, gas injection molding, foam injection molding, etc.), compression molding (e.g., extrusion compression molding), extrusion molding; printing (e.g., three-dimensional printing); and so forth. For example, an injection molding system may be employed that includes a mold within which the polymer composition may be injected. The time inside the injector may be controlled and optimized so that polymer matrix is not pre-solidified. When the cycle time is reached and the barrel is full for discharge, a piston may be used to inject the composition to the mold cavity. Compression molding systems may also be employed. As with injection molding, the shaping of the polymer composition into the desired article also occurs within a mold. The composition may be placed into the compression mold using any known technique, such as by being picked up by an automated robot arm. The temperature of the mold may be maintained at or above the solidification temperature of the polymer matrix for a desired time period to allow for solidification. The molded product may then be solidified by bringing it to a temperature below that of the melting temperature. The resulting product may be de-molded. The cycle time for each molding process may be adjusted to suit the polymer matrix, to achieve sufficient bonding, and to enhance overall process productivity.

Referring to FIGS. 1-6, for example, one particular embodiment of a microneedle assembly 500 is shown in more detail that contains a plurality of microneedles 510 (e.g., array of microneedles) that extend outwardly from a support 520. As indicated above, one or more of the microneedles 510 may be formed from the polymer composition of the present invention. The support 520 may also be formed from the polymer composition, as well as from a rigid or flexible sheet of metal, ceramic, plastic, or other material. The support 520 can vary in thickness to meet the needs of the particular drug delivery application, such as about 1000 micrometers or less, in some embodiments from about 1 to about 500 micrometers, and in some embodiments, from about 10 to about 200 micrometers.

Figure 2:
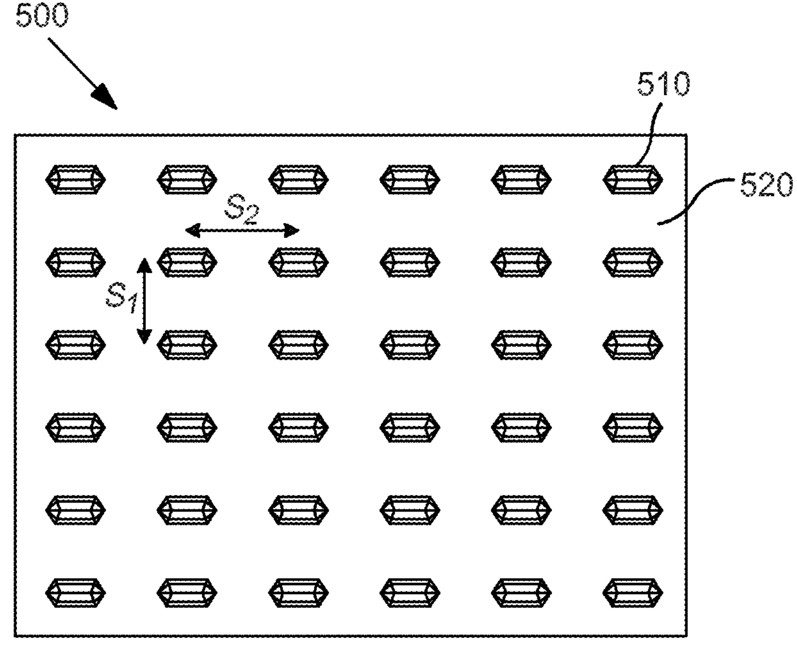
FIG. 2 is a schematic plan view of one embodiment of a microneedle assembly that may be formed according to the present invention.
Figure 3:
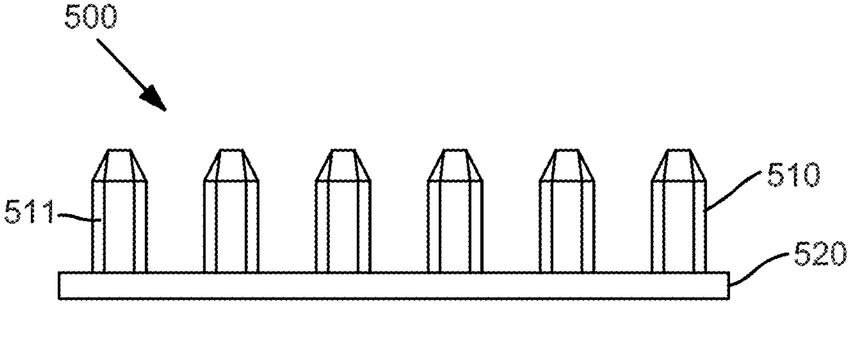
FIG. 3 is a schematic front view of a line of microneedles in the assembly shown in FIG. 2.

The density of the microneedles 510 may vary as desired, such as about 2,000 microneedles per square centimeter ($cm^2$) or more, in some embodiments from about 3,000 to about 25,000 microneedles per $cm^2$, and in some embodiments, from about 5,000 to about 20,000 microneedles per $cm^2$. The number of microneedles 510 used in the assembly 500 may, for example, range from about 500 to about 10,000, in some embodiments from about 2,000 to about 8,000, and in some embodiments, from about 4,000 to about 6,000. The microneedles 510 may be arranged on the support 520 in a variety of patterns. For example, the microneedles may be spaced apart in a uniform manner, such as in a rectangular or square grid or in concentric circles, or they may be arranged in one or more lines. While a variety of arrangements may be employed, a particularly suitable embodiment is shown in FIG. 2 in which the microneedles 510 are arranged in straight, spaced apart lines. The spacing may depend on numerous factors, including height and width of the microneedles 510, as well as the amount and type of substance that is intended to be moved through the microneedles. For example, the spacing between the tips of the microneedles 510 ($S_1$ in FIG. 2) may be from about 20 micrometers or more, in some embodiments about 60 to about 800 micrometers, and in some embodiments, from about 100 to about 600 micrometers, while the spacing between the bases of the microneedles 510 ($S_2$ in FIG. 2) may be from about 50 micrometers or more, in some embodiments about 100 to about 1,000 micrometers, and in some embodiments, from about 200 to about 800 micrometers.

The size and shape of the microneedles 510 may also vary as desired. For example, the microneedles 510 are shown as having a tapering hexagonal shape that contains a tip 611 and a base 612. The base 612 has two substantially parallel sides 621 and 622, with a slight draught angle as indicated in FIG. 5 by $\alpha_1$ up to a transition point 613 at which point the angle increases as indicated in FIG. 5 by $\alpha_2$). Although this example depicts a distinct increase in the angle at the transition point 613, it should be noted that there may be a more gradual increase in the angle than depicted. The draught angle $\alpha_1$ may, for instance, range from about 0 to 20 degrees, in some embodiments from about 0 to 15 degrees, in some embodiments from about 1 to about 15 degrees, and in some embodiments, from about 2 to about 10 degrees. Likewise, the transition point angle $\alpha_2$ may range from about 20 to 70 degrees, in some embodiments from about 20 to 60 degrees, in some embodiments from about 25 to about 55 degrees, and in some embodiments, from about 25 to about 45 degrees. In an alternate embodiment, the ends of the microneedles may be blunted to provide an extended octagonal profile. While the profiles of the microneedles may define extended hexagonal or octagonal shapes, the edges of the profiles may be somewhat rounded depending on the method of manufacture of the microneedles and microneedle arrays.

The tip 611 of each microneedle 510 terminates in an elongate edge. The tip 611 has a width $W_{tip}$ and a length $L_{tip}$. The length of the tip may range from about 5 to about 500 nanometers, in some embodiments from about 10 to about 200 nanometers, and in some embodiments, from about 20 to about 100 nanometers, while the width of the tip may range from about 0.5 to about 5 micrometers, in some embodiments from about 0.6 to about 4 micrometers, and in some embodiments, from about 1 to about 3.5 micrometers. The base 612 has a and a thickness $T_{base}$ and length $L_{base}$, which is greater in length than the tip 611. For instance, the base of the microneedles may have a length of from about 10 to about 1,000 nanometers, in some embodiments from about 20 to about 500 nanometers, and in some embodiments, from about 30 to about 100 nanometers, while the thickness of the base may be from about 5 to about 100 nanometers, in some embodiments from about 10 to about 80 nanometers, and in some embodiments, from about 20 to about 70 nanometers. The cross-sectional length:thickness aspect ratio of the base 612 ($L_{base}$:$T_{base}$) may likewise be relatively high, such as about 2:1 or more, in some embodiments from about 2:1 to about 20:1, and in some embodiments, from about 3:1 to about 10:1. Each microneedle also has an overall height H that is of a length sufficient to penetrate through at least the outermost layer of the epidermis (i.e., stratum corneum), but optionally not so great that they pass through the dermis. For example, the height may be from about 10 to about 1,000 nanometers, in some embodiments from about 20 to about 500 nanometers, and in some embodiments, from about 30 to about 100 nanometers.

The manner in which the microneedle assembly delivers the drug compound may vary as is known in the art. In certain embodiments, for example, the drug compound may be coated onto a surface of the microneedle. Various coating techniques may be employed, such as dipping, spraying, printing (e.g., inkjet printing, spotting, non-contact printing, drop-on-demand piezoelectric micro-dispensing, etc.), and so forth. For example, the microneedles may be dipped into a drug compound reservoir through dip holes that are spaced in accordance with the microneedle array. The microneedles may also be spray coated with the drug compound and then dried with a gas. In yet another embodiment, the microneedles may be coated with the drug compound through a printing technique. Various suitable printing techniques are described, for instance, in U.S. Patent Publication No. 2018/0326726 to Wand, et al., which is incorporated herein by reference in its entirety. For example, a piezoelectric stack actuator may be employed as a driving component that dispenses a fluidic drug compound (or fluid containing the compound) from a pumping chamber though a two-dimensional array of nozzles. The nozzles are aligned with the microneedles so that the dispensed fluid is coated onto a surface thereof.

In embodiments in which the drug compound is coated onto a surface of the microneedles, such as described above, the microneedles may be solid in nature, and thus be free of hollow channels and/or pores for fluid delivery. In such embodiments, the microneedle assembly does not require conventional components (e.g., drug reservoirs, release members, etc.) to drive the delivery of the drug compound. Examples of such solid microneedles are described, for instance, in U.S. Patent Publication No. 2018/0264244 to Meliga, et al., which is incorporated herein in its entirety by reference thereto.

Of course, in alternative embodiments, one or more of the microneedles may contain one or more channels of a certain dimension such that passive capillary flow can drive the delivery of the drug compound. For example, the microneedles may define at least one channel that is in fluidic communication with a drug compound, such as through an aperture of the support. Referring again to FIG. 3, for example, a channel 511 is located on an exterior surface of the microneedles 510. Although shown on an exterior surface, the channel may be located in a variety of different positions, such as in the interior of the microneedle. The dimensions of the channel are specifically selected in the present invention to induce capillary flow of the drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel and directly proportional to the surface tension of the liquid, multiplied by the cosine of the contact angle of the fluid in contact with the material forming the channel. Thus, to facilitate capillary flow, the cross-sectional dimension (e.g., width, diameter, etc.) of the channel may be selectively controlled, with smaller dimensions generally resulting in higher capillary pressure. For example, in some embodiments, the cross-sectional dimension of the channel may range from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio is determined from the average dimensions.

Regardless of the type employed, the microneedle assembly can deliver a controlled volume of a drug compound through the skin. For example, the microneedle assembly may be placed adjacent to the skin of a subject (e.g., human) and pressure may be applied thereto so that the microneedles penetrate into at least the stratum corneum of the epidermis.

If desired, the microneedle assembly may be placed in fluid communication with a reservoir that can initially retain the drug compound, particular in those embodiments which one or more channels are employed. The term “reservoir” generally refers to a designated area or chamber configured to retain a fluidic drug compound. The reservoir may be an open volume space, gel, solid structure, etc. Nevertheless, in most embodiments, the reservoir is a solid matrix through which the drug compound is capable of flowing. The selection of the desired materials for the matrix typically depends on the solubility and diffusivity of the target drug compound and the time during which release is sought. In one embodiment, for example, the solid matrix is generally impermeable to the drug compound, and the material used to form the matrix is selected so that the drug compound is able to diffuse therethrough. In other embodiments, however, the solid matrix may be permeable or semi-permeable to the drug compound so that it can simply flow through its pores. Examples of such solid matrices include porous fiber webs (e.g., woven or nonwoven), apertured films, foams, sponges, etc. Regardless of its particular form, polymeric materials are often used to form the solid matrix, such as silicones, acrylic resins, olefinic polymers (e.g., ethylene vinyl acetate), plasticized polyvinyl acetate/polyvinyl chloride resins, plasticized hydrolyzed polyvinyl alcohol, rubber-based adhesives (e.g., polyisobutylenes extended with a solvent such as mineral oil), plasticized polyvinyl chloride, polyethylene glycols and polypropylene glycols of varying molecular weights, cellulose esters, etc.

A plurality of reservoirs may also be employed in certain embodiments for storing multiple materials for delivery. The reservoirs may be positioned adjacent to each other, either in a vertical or horizontal relationship. For instance, a first reservoir may contain a drug compound and a second reservoir may contain an excipient (e.g., delivery vehicle, such as alcohols, water, etc.; buffering agents; and so forth). In one particular embodiment, for example, the first reservoir may contain a lyophilized powder of the drug compound and the second reservoir may contain an aqueous solution for reconstituting the powder. Alternatively, multiple reservoirs may be employed that each contains a drug compound. The different materials may be mixed prior to delivery.

In certain embodiments, the microneedle assembly and drug reservoir(s) may be integrated together in the form of a transdermal delivery device (e.g., patch). The path may also contain other elements to help maintain the desired flow of the drug compound. For example, the drug reservoir may be in fluid communication with a rate control membrane that helps control the flow rate of the drug compound by modulating its pressure downstream from the reservoir. The rate control membrane can help slow down the flow rate of the drug compound upon its release. Specifically, fluidic drug compounds passing from the drug reservoir to the microneedle assembly may experience a drop in pressure that results in a reduction in flow rate. If this difference is too great, some backpressure may be created that can impede the flow of the compound and potentially overcome the capillary pressure of the fluid through the microfluidic channels. Thus, the use of the rate control membrane can ameliorate this difference in pressure and allow the drug compound to be introduced into the microneedle at a more controlled flow rate. The particular materials, thickness, etc. of the rate control membrane can vary based on multiple factors, such as the viscosity of the drug compound, the desired delivery time, etc. The rate-controlling membrane may, for instance, include a permeable, semi-permeable or microporous material. Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers.

If desired, the transdermal delivery device may contain additional layers or materials that provide various benefits. For example, the assembly may include an adhesive layer that can help facilitate the attachment of the delivery device to a user’s skin during use. Although not required, the adhesive layer is often disposed over the reservoir. The adhesive layer typically employs an adhesive coated onto a backing material. The backing may be made of a material that is substantially impermeable to the drug compound, such as polymers, metal foils, etc. Suitable polymers may include, for instance, polyethylene terephthalate, polyvinylchloride, polyethylene, polypropylene, polycarbonate, polyester, and so forth. The adhesive may be a pressure-sensitive adhesive as is known in the art. Suitable adhesives may include, for instance, solvent-based acrylic adhesives, solvent-based rubber adhesives, silicone adhesives, etc.

A release member may also be positioned adjacent to the microneedle assembly so that it is adjacent to the support of the microneedle assembly and the optional rate control membrane. It should be understood, however, that the release layer need not contact such layers, and that other layers may be in fact be positioned between the release member and the support and/or rate control membrane. Regardless, the release member may contain a material that is substantially impermeable to the drug compound, such as a polymeric material, metal, etc. The material is also desirably hydrophobic. Suitable polymeric materials may include, for instance, polyethylene terephthalate, polyvinylchloride, polyethylene, polypropylene, polycarbonate, polyester, metal foils, and so forth. Because it is generally impermeable, the release member can initially seal the aperture in the support and thus limit the flow of the drug compound therethrough. In this manner, the release member may act as a barrier to the flow of the drug compound and thus inhibits premature leakage. When it is desired to use the delivery device, a force may be applied by the user to at least partially separate the release member, thereby breaking the seal. The separation of the release member may be accomplished in a variety of ways. For instance, a portion of the release member may simply be separate (e.g., detached, ruptured, etc.). Thus, the flow of the drug compound can be induced "passively"—i.e., without the need for conventional active displacement mechanisms, such as liquid pumps, actuators, plungers, finger pressure, etc. This allows the delivery device to be placed on the skin before activation, thereby limiting potential spillage of the drug compound. The passive delivery of the drug compound is also simple and easy to use, which enables it to be used by a wide variety of consumers, not just medical professionals.

There is no particular limitation to the drug compounds that may be delivered using the microneedle assembly of the present invention. Suitable compounds may include, for instance, proteinaceous compounds, such as insulin, immunoglobulins (e.g., IgG, IgM, IgA, IgE), TNF-α, antiviral medications, etc.; polynucleotide agents, such as plasmids, siRNA, RNAi, nucleoside anticancer drugs, vaccines, etc.; small molecule agents, such as alkaloids, glycosides, phenols, etc.; anti-infection agents, hormones, drugs regulating cardiac action or blood flow, pain control; vaccines; and so forth. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents.

The microneedle assembly may be particularly beneficial in delivering high molecular weight drug compounds. The term "high molecular weight" generally refers to compounds having a molecular weight of about 1 kiliDalton ("kDa") or more, in some embodiments about 10 kDa or more, in some embodiments about 20 kDa to about 250 kDa, and in some embodiments, from about greater than about 40 kDa to about 150 kDa. Examples of such high molecular weight compounds include protein therapeutics, which refers to any biologically active proteinaceous compound including, without limitation, natural, synthetic, and recombinant compounds, fusion proteins, peptides, chimeras, and so forth, as well as compounds including the 20 standard amino acids and/or synthetic amino acids.

In one particular embodiment, the drug compound may include a vaccine antigen, which is a substance that, when introduced to the body stimulates an immune response, such as T-cell activation and/or antibody production for prophylaxis against a virus. Vaccine antigens may include natural intact pathogens (e.g., bacterium or virus), a live attenuated virus, or portions and/or subunits of a pathogen, such as a single virus or bacterium protein. Vaccine antigens can also include cancer antigens or fragments thereof. In one particular embodiment, for example, the vaccine antigen may be a coronavirus vaccine antigen that is used for prophylaxis against a coronavirus, such as SARS-CoV-1, SARS-CoV-2, MERS-CoV, etc. Such vaccine antigens may be derived from a coronavirus or other type of virus. Specific examples of such coronavirus vaccine antigens may include, for instance, mRNA-1273 (novel lipid nanoparticle (LNP)-encapsulated mRNA-based vaccine), BNT162 (LNP-encapsulated mRNA-based vaccine), Ad5-nCoV (recombinant adenovirus type-5 vector), ChAdOx1 (adenovirus viral vector capable of producing the spike protein of SARS-CoV-2), bacTRL-Spike (live *Bifidobacterium longum* bacteria that have been engineered to deliver plasmids containing synthetic DNA encoding spike protein from SARS-CoV-2), BCG (prepared from a strain of the attenuated (virulence-reduced) live bovine tuberculosis bacillus, *Mycobacterium bovis*), AdCovid (intranasal vaccine), NVX-CoV2373 (recombinant spike protein nanoparticle), SARS recombinant spike protein plus delta inulin (protein subunit), SARS VLPs S protein and influenza M1 protein, DNA vaccine VRC-SRSDNA015-00-VP (DNA), replicating and/or non-replicating viral vectors express SARS-CoV S (e.g., VEEV replicon particles expressing the SARS-CoV S or LV-SMENP (modified dendritic cells with lentivirus vectors expressing CoV-19 minigene SMENP and immune modulatory genes)), inactivated SARS-CoV-2 virus or viral vector, live attenuated SARS-CoV-2 virus, and so forth.

Other suitable viral vaccine antigens may be derived from and/or used for prophylaxis against adenoviruses, arenaviruses, bunyaviruses, flavirviruses, hantaviruses, hepadnaviruses, herpesviruses, papilomaviruses, paramyxoviruses, parvoviruses, picornaviruses, poxviruses, orthomyxoviruses, retroviruses, reoviruses, rhabdoviruses, rotaviruses, spongiform viruses or togaviruses. Examples of such vaccine antigens may include peptides expressed by viruses, such as CMV, EBV, flu viruses, hepatitis A, B, or C, herpes simplex, HIV, influenza, Japanese encephalitis, measles, polio, rabies, respiratory syncytial, rubella, smallpox, varicella zoster, West Nile, and/or Zika. CMV vaccine antigens include envelope glycoprotein B and CMV pp65; EBV vaccine antigens include EBV EBNAI, EBV P18, and EBV P23; hepatitis vaccine antigens include the S, M, and L proteins of hepatitis B virus, the pre-S antigen of hepatitis B virus, HBCAG DELTA, HBV HBE, hepatitis C viral RNA, HCV NS3 and HCV NS4; herpes simplex vaccine antigens include immediate early proteins and glycoprotein ID, human immunodeficiency virus (HIV) vaccine antigens include gene products of the gag, pol, and env genes such as HIV gp32, HIV gp41, HIV gp120, HIV gp160, HIV P17/24, HIV P24, HIV P55 GAG, HIV P66 POL, HIV TAT, HIV GP36, the Nef protein and reverse transcriptase; human papillomavirus virus (HPV) viral antigens include the L1 protein; influenza vaccine antigens include hemagglutinin and neuraminidase; Japanese encephalitis vaccine antigens include proteins E, M-E, M-E-NS1, NS1, NS1-NS2A and 80% E; malaria vaccine antigens include the *Plasmodium* proteins circumsporozoite (CSP), glutamate dehydrogenase, lactate dehydrogenase, and fructose-bisphosphate aldolase; measles vaccine antigens include the measles virus fusion protein; rabies vaccine antigens include rabies glycoprotein and rabies nucleoprotein; respiratory syncytial vaccine antigens include the RSV fusion protein and the M2 protein; rotaviral vaccine antigens include VP7sc; rubella vaccine antigens include proteins E1 and E2; varicella zoster vaccine antigens include gpI and gpII; and zika vaccine antigens include pre-membrane, envelope (E), Domain III of the E protein, and non-structural proteins 1-5.

In the embodiments described above, the microneedle assembly of the present invention is generally used to deliver a drug compound to a subject. In addition to and/or in lieu of drug delivery, the microneedle assembly may also be employed as a sensor. For example, the microneedle assembly may be used only as a sensor, or in other cases, it may be used as a sensor to determine the dosage of the drug compound to delivery. Regardless, the microneedles may be placed into contact with the skin of a subject and allowed to remain for a period of time sufficient to contact a bodily fluid (e.g., blood) from the subject that contains an analyte of interest. The fluid may be withdrawn and tested. Alternatively, a detection system can be coupled to the microneedle assembly, such as incorporated on an external surface of the microneedles (e.g., solid microneedles) or within the interior of the microneedles (e.g., microneedles with hollow channels), so that the fluid can simply be allowed to contact the microneedles for testing. Various examples of such sensors are known in the art and described, for instance, in U.S. Patent Publication Nos. 2020/0015751 to Chickering, et al. and 2013/0225956 to Huang, et al., which are incorporated herein in their entirety by reference thereto.

Examples of target analytes that the sensor may be used to detect include, but are not limited to, pH or metal ions, proteins, nucleic acids (e.g., DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, e.g., legal prescription levels of drugs such as coumadin, other drugs such as nicotine, or illegal drugs such as cocaine. Further examples of analytes include those indicative of disease, such as cancer specific markers such as CEA and PSA, viral and bacterial antigens, and autoimmune indicators, such as antibodies to double stranded DNA. Still other conditions include exposure to elevated carbon monoxide, which could be from an external source or due to sleep apnea, too much heat (important in the case of babies whose internal temperature controls are not fully self-regulating) or from fever. Other potentially suitable analytes include various pathogens, such as bacteria or viruses, and/or markers produced by such pathogens. As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the withdrawn fluid may be determined in certain cases.

The particular detection system used in combination with the microneedle assembly to detect the analyte can vary as understood by those skilled in the art. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasielectric light scattering; polarimetry; refractometry; chemical indicators such as dyes; or turbidity measurements, including nephelometry. In one particular embodiment, for instance, the sensor may rely upon electrochemical impedance for detection and thus include at least one working electrode, which is typically positioned on, within, or otherwise in fluidic contact with a first microneedle. For example, the working electrode may be a metal (e.g., gold) that is deposited on a surface of the microneedle. The sensor may also include at least one reference electrode positioned on, within, or otherwise in fluidic contact with a second microneedle and/or at least one counter electrode positioned on, within and/or otherwise in fluidic contact with a third microneedle. For example, the reference and counter electrodes may also be made of a metal (e.g., gold) deposited on a surface of respective microneedles. Impedance values may be detected to evaluate the concentration of the analyte. If desired, the sensitivity of the detection system can be enhanced through the accumulation of a trace amount of target molecules at the electrode. For specificity, the microneedles (e.g., working electrode) may be subjected to surface modification, such as with an enzyme, an antibody, an aptamer, a single-chain variable fragment (ScFv), a carbohydrate, and a combination thereof. In one embodiment, for instance, the working electrodes may be modified with glucose oxidase (GOx) for glucose detection.

The present invention may be better understood with reference to the following examples.

Test Methods

Melt Viscosity: The melt viscosity (Pa-s) may be determined in accordance with ISO Test No. 11443:2005 at a shear rate of 400 $s^{-1}$ or 1,000 $s^{-1}$ and temperature 15° C. above the melting temperature (e.g., about 350° C.) using a Dynisco LCR7001 capillary rheometer. The rheometer orifice (die) had a diameter of 1 mm, length of 20 mm, L/D ratio of 20.1, and an entrance angle of 180°. The diameter of the barrel was 9.55 mm+0.005 mm and the length of the rod was 233.4 mm.

Melting Temperature: The melting temperature ("Tm") may be determined by differential scanning calorimetry ("DSC") as is known in the art. The melting temperature is the differential scanning calorimetry (DSC) peak melt temperature as determined by ISO Test No. 11357-2:2013. Under the DSC procedure, samples were heated and cooled at 20° C. per minute as stated in ISO Standard 10350 using DSC measurements conducted on a TA Q2000 Instrument.

Deflection Temperature Under Load ("DTUL"): The deflection under load temperature may be determined in accordance with ISO Test No. 75-2:2013 (technically equivalent to ASTM D648-07). More particularly, a test strip sample having a length of 80 mm, thickness of 10 mm, and width of 4 mm may be subjected to an edgewise three-point bending test in which the specified load (maximum outer fibers stress) was 1.8 Megapascals. The specimen may be lowered into a silicone oil bath where the temperature is raised at 2° C. per minute until it deflects 0.25 mm (0.32 mm for ISO Test No. 75-2:2013).

Tensile Modulus, Tensile Stress, and Tensile Elongation: Tensile properties may be tested according to ISO Test No. 527:2012 (technically equivalent to ASTM D638-14). Modulus and strength measurements may be made on the same test strip sample having a length of 80 mm, thickness of 10 mm, and width of 4 mm. The testing temperature may be 23° C., and the testing speeds may be 1 or 5 mm/min.

Flexural Modulus, Flexural Stress, and Flexural Elongation: Flexural properties may be tested according to ISO Test No. 178:2010 (technically equivalent to ASTM D790-10). This test may be performed on a 64 mm support span. Tests may be run on the center portions of uncut ISO 3167 multi-purpose bars. The testing temperature may be 23° C. and the testing speed may be 2 mm/min.

Unnotched and Notched Charpy Impact Strength: Charpy properties may be tested according to ISO Test No. ISO 179-1:2010) (technically equivalent to ASTM D256-10, Method B). This test may be run using a Type 1 specimen size (length of 80 mm, width of 10 mm, and thickness of 4 mm). When testing the notched impact strength, the notch may be a Type A notch (0.25 mm base radius). Specimens may be cut from the center of a multi-purpose bar using a single tooth milling machine. The testing temperature may be 23° C.

Example 1

Samples 1-5 and a Control sample are formed for use in a microneedle assembly. The samples contained various combinations of a liquid crystalline polymer (LCP 1 of LCP 2), talc (TALC 1 or TALC 2), and/or polytetrafluoroethylene (PTFE). LCP 1 is formed from 60% HBA, 4% HNA, 18% BP, and 18% TA. LCP 2 is formed from 48% HNA, 2% HBA, 25% BP, and 25% TA. TALC 1 had a median particle size of 4 micrometers and TALC 2 had a median particle size of 1 micrometer. Compounding was performed using an 18-mm single screw extruder. Samples are injection molded into plaques (60 mm×60 mm). The formulations are set forth below.

| | Control | Sample 1 | Sample 2 | Sample 3 | Sample 4 | Sample 5 |
|---|---|---|---|---|---|---|
| LCP 1 | 100 | — | — | — | — | — |
| LCP 2 | — | 100 | 79 | 89 | 79 | 99 |
| TALC 1 | — | — | 21 | 11 | — | — |
| TALC 2 | — | — | — | — | 21 | — |
| PTFE | — | — | — | — | — | 1 |

Samples 1-5 were tested for thermal and mechanical properties. The results are set forth below.

| | Control | Sample 1 | Sample 2 | Sample 3 | Sample 4 | Sample 5 |
|---|---|---|---|---|---|---|
| Melt Viscosity at 380° C., 1,000 $s^{-1}$ (Pa-s) | — | — | 25.2 | 25.1 | 24.2 | 23.6 |
| Melt Viscosity at 380° C., 400 $s^{-1}$ (Pa-s) | — | 47.0 | 34.6 | 35.0 | 31.5 | 37.8 |
| Melt Viscosity at 300° C., 400 $s^{-1}$ (Pa-s) | 67.0 | — | — | — | — | — |
| Melting Temperature, $1^{st}$ Heat (° C.) | 280 | 350 | 346.51 | 347.09 | 342.18 | 344.39 |
| DTUL at 1.8 MPa (° C.) | 168 | 290 | 282 | 291 | 280 | — |
| Charpy Notched Impact Strength (kJ/$m^2$) | — | — | 6 | 16.4 | 6.5 | — |
| Tensile Strength (MPa) | 148 | 110 | 142 | 154 | 147 | — |
| Tensile Modulus (MPa) | 7,800 | 7,443 | 7,985 | 7,917 | 9,917 | — |
| Tensile Elongation (%) | 5.70 | 1.78 | 3.47 | 3.08 | 2.33 | — |
| Flexural Strength (MPa) | — | — | 154 | 164 | 167 | — |
| Flexural Modulus (MPa) | | | 9,182 | 9,474 | 10,918 | — |
| Flexural Elongation (%) | | | >3.5 | 3.44 | 2.77 | — |

Example 2

Samples 6-10 are formed for use in a microneedle assembly. The samples contained various combinations of a liquid crystalline polymer (LCP 2), talc (TALC 1 or TALC 2), and/or polytetrafluoroethylene (PTFE). LCP is formed from 48% HNA, 2% HBA, 25% BP, and 25% TA. Compounding was performed using an 18-mm single screw extruder. Samples are injection molded into plaques (60 mm×60 mm). The formulations are set forth below.

| | Sample 6 | Sample 7 | Sample 8 | Sample 9 | Sample 10 |
|---|---|---|---|---|---|
| LCP 2 | 78 | 88 | 100 | 58 | 58 |
| TALC 1 | — | — | — | 41 | — |
| TALC 2 | 21 | 11 | — | — | 41 |
| PTFE | 1 | 1 | — | 1 | 1 |

Samples 6-10 were tested for thermal and mechanical properties. The results are set forth below.

| | Sample 6 | Sample 7 | Sample 8 | Sample 9 | Sample 10 |
|---|---|---|---|---|---|
| Melt Viscosity at 380° C., 1,000 $s^{-1}$ (Pa-s) | 27.1 | 29.2 | 23.3 | 40.9 | 41.1 |
| Melt Viscosity at 380° C., 400 $s^{-1}$ (Pa-s) | 37.4 | 40.1 | 32.3 | 57.7 | 64.7 |
| Melting Temperature, $1^{st}$ Heat (° C.) | 343.06 | 345.36 | 345.14 | 339.63 | 341.71 |
| DTUL at 1.8 MPa (° C.) | — | 286 | — | 272 | 272 |
| Charpy Notched Impact Strength ($kJ/m^2$) | — | 19.5 | — | 2.2 | 2.0 |
| Tensile Strength (MPa) | — | 155 | — | 97 | 89 |
| Tensile Modulus (MPa) | — | 9,247 | — | 9,787 | 10,172 |
| Tensile Elongation (%) | — | 2.32 | — | 2 | 1.33 |
| Flexural Strength (MPa) | — | 169 | — | 133 | 127 |
| Flexural Modulus (MPa) | — | 10,005 | — | 10,390 | 10,859 |
| Flexural Elongation (%) | — | 3.13 | — | 2.45 | 1.82 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A microneedle assembly comprising at least one microneedle extending outwardly from a support, wherein the microneedle includes a polymer composition containing a thermoplastic polymer having a melting temperature of about 300° C. or more, wherein the polymer composition exhibits a melt viscosity of about 100 Pa-s or less as determined in accordance with ISO Test No. 11443:2014 at a shear rate at a shear rate of 1,000 seconds-1 and temperature of about 30° C. above the melting temperature, wherein a ratio of the deflection temperature under load as determined in accordance with ISO Test No. 75-2:2013 at a load of 1.8 Megapascals to the melting temperature is from 0.75 to 1, and further wherein the polymer composition exhibits a tensile elongation of about 5% or less as determined at in accordance with ISO Test No. 527:2012 at a temperature of about 23° C.

2. The microneedle assembly of claim 1, wherein the polymer composition exhibits a melt viscosity of about 150 Pa-s or less as determined in accordance with ISO Test No. 11443:2014 at a shear rate at a shear rate of 400 seconds-1 and temperature of about 30° C. above the melting temperature.

3. The microneedle assembly of claim 1, wherein the polymer composition exhibits a deflection temperature under load of about 160° C. or more as determined in accordance with ISO Test No. 75-2:2013 at a load of 1.8 Megapascals.

4. The microneedle assembly of claim 3, wherein the ratio of the deflection temperature under load to the melting temperature is from about 0.75 to about 0.95.

5. The microneedle assembly of claim 1, wherein the polymer composition exhibits a tensile modulus of about 7,000 MPa or more as determined in accordance with ISO Test No. 527:2012 at a temperature of about 23° C.

6. The microneedle assembly of claim 1, wherein the thermoplastic polymer includes a polyarylene sulfide, polyamide, polyaryleneketone, liquid crystalline polymer, or a combination thereof.

7. The microneedle assembly of claim 1, wherein the thermoplastic polymer includes a liquid crystalline polymer.

8. The microneedle assembly of claim 7, wherein the liquid crystalline polymer contains repeating units derived from one or more aromatic dicarboxylic acids, one or more aromatic hydroxycarboxylic acids, or a combination thereof.

9. The microneedle assembly of claim 8, wherein the aromatic hydroxycarboxylic acids include 4-hydroxybenzoic acid, 6-hydroxy-2-naphthoic acid, or a combination thereof.

10. The microneedle assembly of claim 8, wherein the aromatic hydroxycarboxylic acids include terephthalic acid, isophthalic acid, 2,6-naphthalenedicarboxylic acid, or a combination thereof.

11. The microneedle assembly of claim 8, wherein the liquid crystalline polymer further contains repeating units derived from one or more aromatic diols.

12. The microneedle assembly of claim 11, wherein the aromatic diols include hydroquinone, 4,4'-biphenol, or a combination thereof.

13. The microneedle assembly of claim 7, wherein the liquid crystalline polymer is wholly aromatic.

14. The microneedle assembly of claim 7, wherein the liquid crystalline polymer contains repeating units derived from naphthenic hydroxycarboxylic and/or dicarboxylic acids in an amount of about 10 mol. % or more.

15. The microneedle assembly of claim 7, wherein the liquid crystalline polymer contains repeating units derived from 6-hydroxy-2-naphthoic acid in an amount of about 30 mol. % or more.

16. The microneedle assembly of claim 1, wherein thermoplastic polymers constitute from about 30 wt. % to about 99 wt. % of the polymer composition.

17. The microneedle assembly of claim 1, wherein the polymer composition further comprises a mineral filler.

18. The microneedle assembly of claim 17, wherein the mineral filler is in the form of particles.

19. The microneedle assembly of claim 18, wherein the particles have a median size of about 10 micrometers or less.

20. The microneedle assembly of claim 18, wherein the particles have a median size of from about 0.6 to about 2.5 micrometers.

21. The microneedle assembly of claim 18, wherein the particles include talc.

22. The microneedle assembly of claim 1, wherein the polymer composition further comprises a tribological additive material.

23. The microneedle assembly of claim 22, wherein the tribological additive material includes a fluoropolymer.

24. The microneedle assembly of claim 1, wherein the assembly includes a plurality of microneedles arranged in an array on the support.

25. The microneedle assembly of claim 1, wherein the microneedle has a tip and base.

26. The microneedle assembly of claim 25, wherein the tip has a length of from about 5 to about 500 nanometers and a width of from about 0.5 to about 5 micrometers.

27. The microneedle assembly of claim 25, wherein the base has a length of from about 10 to about 1,000 nanometers and a thickness of from about 5 to about 100 micrometers.

28. The microneedle assembly of claim 1, wherein the microneedle has a height of from about 10 to about 1,000 nanometers.

29. The microneedle assembly of claim 1, wherein the assembly is configured to deliver a drug compound.

30. The microneedle assembly of claim 29, wherein the drug compound includes a proteinaceous compound, polynucleotide agent, vaccine, small molecule agent, anti-infection agent, hormone, drug regulating cardiac action or blood flow, or a combination thereof.

31. The microneedle assembly of claim 29, wherein the drug compound has a molecular weight of about 1 kDa or more.

32. The microneedle assembly of claim 29, wherein the drug compound includes a viral vaccine antigen.

33. The microneedle assembly of claim 32, wherein the vaccine antigen is a coronavirus vaccine antigen.

34. The microneedle assembly of claim 33, wherein the vaccine antigen is a viral vector, live attenuated virus, or an inactivated virus.

35. The microneedle assembly of claim 33, wherein the coronavirus vaccine antigen includes mRNA-1273, BNT162, Ad5-nCOV, ChAdOx1, bacTRL-Spike, BCG, AdCovid, NVX-CoV2373, LV-SMENP, SARS recombinant spike protein plus delta inulin, SARS VLPs S protein and influenza M1 protein, DNA vaccine VRC-SRSDNA015-00-VP, VEEV replicon particles expressing the SARS-COV S, inactivated SARS-CoV-2 virus or viral vector, live attenuated SARS-CoV-2 virus, or a combination thereof.

36. The microneedle assembly of claim 32, wherein the viral vaccine antigen is derived from and/or used for prophylaxis against adenoviruses, arenaviruses, bunyaviruses, flavirviruses, hantaviruses, hepadnaviruses, herpesviruses, papilomaviruses, paramyxoviruses, parvoviruses, picornaviruses, poxviruses, orthomyxoviruses, retroviruses, reoviruses, rhabdoviruses, rotaviruses, spongiform viruses, togaviruses, or a combination thereof.

37. The microneedle assembly of claim 29, wherein the drug compound is coated onto a surface of the microneedle.

38. The microneedle assembly of claim 37, wherein the microneedle is solid.

39. The microneedle assembly of claim 29, wherein the microneedle contains at least one channel through which the drug compound is capable of flowing.

40. A transdermal delivery device comprising the microneedle assembly of claim 39 and a drug reservoir in fluid communication with the channel, wherein the drug compound is located within a reservoir.

41. The transdermal delivery device of claim 40, further comprising an additional reservoir containing an excipient.

42. A method for delivering a drug compound to a subject, the method comprising:

placing the transdermal delivery device of claim 1 adjacent to the skin of a subject;

penetrating a stratum corneum of the skin with the microneedle; and transporting the drug compound from the microneedle and across the stratum corneum.

43. The method of claim 42, wherein the drug compound has a molecular weight of about 1 kDa or more.

44. The method of claim 42, wherein the drug compound includes a viral vaccine antigen.

45. The method of claim 44, wherein the viral vaccine antigen includes a coronavirus vaccine antigen.

46. The method of claim 45, wherein the coronavirus vaccine antigen includes mRNA-1273, BNT162, Ad5-nCOV, ChAdOx1, bacTRL-Spike, BCG, AdCovid, NVX-CoV2373, LV-SMENP, SARS recombinant spike protein plus delta inulin, SARS VLPs S protein and influenza M1 protein, DNA vaccine VRC-SRSDNA015-00-VP, VEEV replicon particles expressing the SARS-COV S, inactivated SARS-CoV-2 virus or viral vector, live attenuated SARS-CoV-2 virus, or a combination thereof.

47. A method for detecting a target analyte in a subject, the method comprising:

placing the transdermal delivery device of claim 1 adjacent to the skin of a subject;

penetrating a stratum corneum of the skin with the microneedle so that the microneedle contacts a bodily fluid of the subject; and detecting the presence of the analyte within the bodily fluid.

48. The method of claim 47, wherein the bodily fluid is blood.

49. The method of claim 47, wherein the analyte is detected on a surface of the microneedle.

50. The method of claim 49, wherein the microneedle is solid.

51. The method of claim 47, wherein the analyte is glucose.

52. The method of claim 47, wherein the bodily fluid is withdrawn from the subject through the microneedle.

* * * * *